(12) United States Patent
Zhou et al.

(10) Patent No.: US 6,756,098 B2
(45) Date of Patent: Jun. 29, 2004

(54) PRESSURE SENSITIVE ADHESIVES WITH A FIBROUS REINFORCING MATERIAL

(75) Inventors: Zhiming Zhou, Woodbury, MN (US); Albert I. Everaerts, Oakdale, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/180,784

(22) Filed: Jun. 25, 2002

(65) Prior Publication Data

US 2002/0187294 A1 Dec. 12, 2002

Related U.S. Application Data

(63) Continuation-in-part of application No. 09/764,478, filed on Jan. 17, 2001, now abandoned.

(51) Int. Cl.$^7$ ................................. B32B 9/00
(52) U.S. Cl. .................. 428/40.1; 428/40.2; 428/41.3; 428/41.5; 428/41.9; 428/42.1; 428/212; 428/220
(58) Field of Search ............... 428/40.1, 40.2, 428/41.3, 41.5, 41.9, 42.1, 212, 220

(56) References Cited

U.S. PATENT DOCUMENTS

| | | | |
|---|---|---|---|
| 3,062,683 A | 11/1962 | Kalleberg et al. | |
| 3,770,558 A | * 11/1973 | Stahl ........................... | 428/40 |
| 3,825,379 A | 7/1974 | Lohkamp et al. | |
| 3,849,241 A | 11/1974 | Butin et al. | |
| 4,024,312 A | 5/1977 | Korpman | |
| 4,554,324 A | 11/1985 | Husman et al. | |
| 4,557,960 A | * 12/1985 | Vernon ......................... | 428/40 |
| 4,588,258 A | 5/1986 | Hoopman | |
| 4,833,179 A | 5/1989 | Young et al. | |
| 4,952,650 A | 8/1990 | Young et al. | |
| 5,175,030 A | 12/1992 | Lu et al. | |
| 5,176,952 A | 1/1993 | Joseph et al. | |
| 5,183,597 A | 2/1993 | Lu | |
| 5,215,087 A | 6/1993 | Anderson et al. | |
| 5,232,770 A | 8/1993 | Joseph | |
| 5,238,733 A | 8/1993 | Joseph et al. | |
| 5,248,455 A | 9/1993 | Joseph et al. | |
| 5,258,220 A | 11/1993 | Joseph | |
| 5,292,844 A | 3/1994 | Young et al. | |
| 5,336,552 A | 8/1994 | Strack et al. | |
| 5,374,698 A | 12/1994 | Young et al. | |
| 5,382,400 A | 1/1995 | Pike et al. | |
| 5,382,451 A | 1/1995 | Johnson et al. | |
| 5,409,189 A | 4/1995 | Luhmann | |
| 5,464,916 A | 11/1995 | Young et al. | |
| 5,491,012 A | 2/1996 | Luhmann et al. | |
| 5,498,463 A | 3/1996 | McDowall et al. | |
| 5,507,464 A | 4/1996 | Hamerski et al. | |
| 5,512,358 A | 4/1996 | Shawver et al. | |
| 5,512,612 A | 4/1996 | Brown et al. | |
| 5,516,581 A | 5/1996 | Kreckel et al. | |
| 5,545,464 A | 8/1996 | Stokes | |
| 5,626,931 A | 5/1997 | Luhmann | |
| 5,626,955 A | 5/1997 | Goetz et al. | |
| 5,672,402 A | 9/1997 | Kreckel et al. | |
| 5,695,868 A | 12/1997 | McCormack | |
| 5,696,199 A | 12/1997 | Senkus et al. | |
| 5,725,923 A | 3/1998 | Luhmann | |
| 5,728,786 A | 3/1998 | Young et al. | |
| 5,804,610 A | 9/1998 | Hamer et al. | |
| 5,897,949 A | 4/1999 | Luhmann et al. | |
| 5,921,514 A | 7/1999 | Schumann | |
| 5,925,459 A | 7/1999 | Zimmermann et al. | |
| 5,928,747 A | 7/1999 | Luhmann et al. | |
| 5,984,247 A | 11/1999 | Luhmann et al. | |
| 5,989,708 A | 11/1999 | Kreckel | |
| 6,001,471 A | 12/1999 | Bries et al. | |
| 6,004,642 A | 12/1999 | Langford | |
| 6,045,895 A | 4/2000 | Hyde et al. | |
| 6,063,838 A | 5/2000 | Patnode et al. | |
| 6,107,219 A | 8/2000 | Joseph et al. | |
| 6,171,985 B1 | 1/2001 | Joseph et al. | |
| 6,197,845 B1 | * 3/2001 | Janssen ....................... | 523/111 |
| 6,285,001 B1 | 9/2001 | Fleming et al. | |

FOREIGN PATENT DOCUMENTS

| | | |
|---|---|---|
| DE | 33 31 016 C2 | 8/1983 |
| WO | WO 95/06691 | 3/1995 |
| WO | WO 96/25469 | 8/1996 |
| WO | WO 97/23577 | 7/1997 |
| WO | WO 98/19852 | 5/1998 |

OTHER PUBLICATIONS

Wente et al., "Manufacture of Superfine Organic Fibers", Naval Research Laboratory, Report 4364, May 25, 1954, pp. 1–15.

Wente, "Superfine Thermoplastic Fibers", Industrial and Engineering Chemistry, vol. 48, No. 8, Aug. 1956, pp. 1342–1346.

Article, "Mixing in Single–Screw Extruders", *Mixing in Polymer Processing*, edited by Chris Rauwendaal (Marcel Dekker Inc.: New York (1991), pp. 129, 176–177, and 185–186.

\* cited by examiner

*Primary Examiner*—Nasser Ahmad
(74) *Attorney, Agent, or Firm*—Colene H. Blank

(57) ABSTRACT

This invention is directed to a fiber reinforced adhesive composition comprising a pressure sensitive adhesive matrix and a fibrous reinforcing material within the pressure sensitive adhesive matrix. The adhesive composition has a yield strength and a tensile strength. The tensile strength is at least about 150% of the yield strength. Generally, the adhesive composition exhibits these properties at least 50% elongation when measured according to ASTM D 882-97 at a crosshead speed of 12 inches/minute (30 centimeters/minute).

27 Claims, No Drawings

US 6,756,098 B2

PRESSURE SENSITIVE ADHESIVES WITH A FIBROUS REINFORCING MATERIAL

CROSS REFERENCE TO RELATED APPLICATION

This application is a continuation-in-part of U.S. application Ser. No. 09/764,478, filed Jan. 17, 2001, now abandoned.

FIELD OF THE INVENTION

The present invention relates to pressure sensitive adhesive compositions. In particular, the invention discloses fiber reinforced pressure sensitive adhesives and methods for their preparation and use.

BACKGROUND OF THE INVENTION

Pressure sensitive adhesives are generally characterized by their properties. Pressure sensitive adhesives are well known to one of ordinary skill in the art to possess properties including the following: (1) aggressive and permanent tack, (2) adherence to a substrate with no more than finger pressure, (3) sufficient ability to hold onto an adherend, and (4) sufficient cohesive strength to be removed cleanly from the adherend. Many pressure sensitive adhesives must satisfy these properties under an array of different stress rate conditions. Additives may be included in the pressure sensitive adhesive to optimize the characteristics of the pressure sensitive adhesive.

In particular systems, the additive improves the cohesive strength of the pressure sensitive adhesives, yet the tack is reduced. For example, a non-tacky additive may be mixed with a pressure sensitive adhesive, reducing the tack of the mixture (as compared to the tack of the pressure sensitive adhesive without the additive). In a specific example, thermoplastic polymers have been added to styrene block copolymer adhesives to reduce the tack of the resulting pressure sensitive adhesives. However, to avoid loss of tack when enhancing the pressure sensitive adhesive's cohesive strength, care must be taken in choosing an additive.

U.S. Pat. No. 6,063,838 discloses a pressure sensitive adhesive comprising a blend of at least two components, wherein the first component is at least one pressure sensitive adhesive and the second component is at least one thermoplastic material, wherein the components form a blended composition having more than one domain and, wherein one domain is substantially continuous (generally, the pressure sensitive adhesive) and the other domain is substantially fibrillous to schistose (generally, the thermoplastic material). The blended pressure sensitive adhesives of the U.S. Pat. No. 6,063,838 patent provide adhesives having one or more of the following properties including: (1) a peel adhesion greater than and shear strength similar to that of the pressure sensitive adhesive component if used alone, (2) a shear strength greater than and peel adhesion similar to that of the pressure sensitive adhesive component if used alone, (3) an anisotropic peel adhesion, (4) an anisotropic shear strength, (5) a tensile stress in the down-web direction that is at least two times greater than the tensile stress in the cross-web direction for all elongations up to the break elongation, and (6) a resistance to impact shear that is at least two times greater than that of the pressure sensitive adhesive component if used alone.

What is desired is an adhesive composition that has improved cohesive strength without losing the tackiness indicative of a pressure sensitive adhesive. In conjunction, it is desirable to create an adhesive composition that is removable from a substrate with ease without losing the tackiness indicative of a pressure sensitive adhesive. Additionally, a stretch removable adhesive composition is desirable.

SUMMARY OF THE INVENTION

This invention is directed to a fiber reinforced adhesive composition comprising a pressure sensitive adhesive matrix and a fibrous reinforcing material within the pressure sensitive adhesive matrix. The fiber reinforced adhesive composition of the invention allows for an improved cohesive strength over the pressure sensitive adhesive alone, yet the tack of the pressure sensitive adhesive remains substantially unreduced.

The adhesive composition has a yield strength and a tensile strength. In one embodiment, the tensile strength is about 0.7 MPa or greater. In another embodiment, the tensile strength is at least about 150% of the yield strength when tested according to ASTM D 882-97 at a crosshead speed of 12 inches/minute (30 centimeters/minute). In one embodiment, the adhesive composition exhibits at least 50% elongation when measured according to ASTM D 882-97 at a crosshead speed of 12 inches/minute (30 centimeters/minute). In certain embodiments, the fibrous reinforcing material comprises substantially continuous fibers within the pressure sensitive adhesive matrix. Additionally, in preferred embodiments, the fiber reinforced adhesive composition will display stretch removable characteristics and easy removal from a substrate.

In addition, the invention is directed to a method for making a fiber reinforced adhesive. The method comprises forming a mixture comprising a pressure sensitive adhesive with a reinforcing material capable of forming fibers when subjected to an elongating shear force, and subjecting the mixture to the elongating shear force.

In this application, the following terms are defined as follows, unless otherwise stated:

"Stretch removable" means that a pressure sensitive adhesive, when pulled and elongated (preferably from a substrate surface at a rate of 30 centimeters/minute and at an angle of no greater than 45°), detaches from a substrate surface without significant damage to the substrate surface (e.g. tearing), and without leaving a significant residue, preferably that which is visible to the unaided human eye on the substrate.

"Substantially continuous" means that for an at least 0.5 centimeter length sample of the adhesive composition taken in the machine direction, at least 50% of the fibers present in the sample are continuous (i.e. unbroken).

"Tensile strength" is the maximum tensile strength at break when tested according to ASTM D 882-97 at a crosshead speed of 12 inches/minute (30 centimeters/minute).

DETAILED DESCRIPTION OF THE INVENTION

The present invention is directed to a fiber reinforced adhesive composition comprising a pressure sensitive adhesive matrix and a reinforcing material within the pressure sensitive adhesive matrix. In one embodiment, the fiber reinforced adhesive composition of the present invention has improved cohesive strength, as represented by a higher tensile strength of the fiber reinforced adhesive composition as compared to the pressure sensitive adhesive without the reinforcing material. Additionally, in a preferred embodiment, the adhesive composition is stretch removable. The adhesive composition of the invention has these properties while maintaining substantially unreduced tack properties in many embodiments.

In another embodiment, the adhesive composition has a lower flow, or lower creep, under certain conditions than an adhesive without the reinforcement material. Creep or flow during storing or transport can be very detrimental to adhesive systems. This is particularly true when adhesive systems are delivered in roll, tape or sheet form. The adhesive within a roll of tape or a stack of sheets is subject to pressure from the weight of the layers above it and can flow or creep. This flow or creep can result in adhesive oozing out of the side of the roll or stack making the edge tacky and picking up dirt or other debris or causing adjacent rolls or stacks to stick together. If the liner or low adhesion backsize (LAB) of the roll of tape or stack of sheets has microstructuring, adhesive flow or creep into the microstructuring can result in a build-up in adhesion forces, even to the point that the tape, roll or stack cannot be unwound. The flow of the adhesive under normal conditions typically leads to edge residue, black rings (on skin) and adherand surface feature encapsulation (for example hair on skin). Reinforcement of the adhesive decreases or prevents this flow or creep.

In the present invention, the adhesive composition has a yield strength. In certain embodiments, the yield strength is no less than about 0.1 MPa when measured according to ASTM D 882-97 at a crosshead speed of 12 inches/minute (30 centimeters/minute). In specific embodiments, the yield strength is no less than about 0.2 MPa when measured according to ASTM D 882-97 at a crosshead speed of 12 inches/minute (30 centimeters/minute).

Additionally, the adhesive composition has a tensile strength of at least about 150% of the yield strength when measured according to ASTM D 882-97 at a crosshead speed of 12 inches/minute (30 centimeters/minute). In certain embodiments, the tensile strength is about 0.7 MPa or greater when measured according to ASTM D 882-97 at a crosshead speed of 12 inches/minute (30 centimeters/minute). In specific embodiments, the tensile strength is about 0.8 MPa or greater when measured according to ASTM D 882-97 at a crosshead speed of 12 inches/minute (30 centimeters/minute). The adhesive composition may have a tensile strength of at least about two times greater than the tensile strength of the pressure sensitive adhesive alone when measured according to ASTM D 882-97 at a crosshead speed of 12 inches/minute (30 centimeters/minute).

For preferred embodiments, the elongation at break for the adhesive composition is at least about 50% when measured according to ASTM D 882-97 at a crosshead speed of 12 inches/minute (30 centimeters/minute), preferably more than about 200%, and may be higher than about 300%. In some embodiments the elongation at break is in excess of about 800%.

Additionally, in preferred embodiments, the amount of force required to remove the adhesive composition from a polypropylene substrate at an angle of between 15° and 35° is less than about 20 Newtons/decimeter. This low removal force permits facile removal of the adhesive composition from a substrate. In certain embodiments, the force necessary to remove the adhesive composition from a substrate at such an angle is as low as about 7 Newtons/decimeter.

In some embodiments, the adhesive composition does not flow more than 13 micrometers after 24 hours, for example no more than 10 micrometers after 24 hours at 70° C. according to the Accelerated Aging Test detailed in the Examples section below. In certain embodiments, the adhesive composition flows not more than 8 micrometers after 24 hours at 70° C. according to the Accelerated Aging Test detailed in the Examples section below. Flow of an adhesive is the natural movement of a fluid adhesive as opposed to propagation of a crack.

In some embodiments, the fiberous reinforcing material lowers compliance and increases viscosity from the adhesive without the fiberous reinforcement. For example, the adhesive has a creep compliance of less than $7 \times 10^{-4}$ $Pa^{-1}$. In other embodiments the adhesive has a creep compliance of less than $5 \times 10^{-4}$ $Pa^{-1}$, for example less than $3 \times 10^{-4}$ $Pa^{-1}$ and in further example less than $2 \times 10^{-4}$ $Pa^{-1}$. Such an adhesive may additionally have a viscosity greater than $1 \times 10^6$ Pa·s, for example greater than $5 \times 10^6$ Pa·s and in further example greater than $1 \times 10^7$ Pa·s.

Pressure Sensitive Adhesive

Any suitable pressure sensitive adhesive composition can be used for this invention. The pressure sensitive adhesive component can be any material that has pressure sensitive adhesive properties. Furthermore, the pressure sensitive adhesive component can be a single pressure sensitive adhesive or the pressure sensitive adhesive can be a combination of two or more pressure sensitive adhesives.

Pressure sensitive adhesives useful in the present invention include, for example, those based on natural rubbers, synthetic rubbers, styrene block copolymers, polyvinyl ethers, poly (meth)acrylates (including both acrylates and methacrylates), polyolefins, and silicones.

The pressure sensitive adhesive may be inherently tacky. If desired, tackifiers may be added to a base material to form the pressure sensitive adhesive. Useful tackifiers include, for example, rosin ester resins, aromatic hydrocarbon resins, aliphatic hydrocarbon resins, and terpene resins. Other materials can be added for special purposes, including, for example, oils, plasticizers, antioxidants, ultraviolet ("UV") stabilizers, hydrogenated butyl rubber, pigments, and curing agents. In certain embodiments, for example embodiments with lower flow or creep, the pressure sensitive adhesive matrix has an inherent viscosity of at least about 0.45 dl/g. The inherent viscosity is measured on a solution of the adhesive in a solvent at 25° C. The difference in out-flow time between the polymer solution and solvent is measured using a Schott Gerate capillary viscometer to find the relative viscosity. For example, for acrylic adhesives, the solvent is ethyl acetate and the polymer is at a concentration of 0.1 g/dL. The inherent viscosity is then calculated as the natural log of the relative viscosity over the concentration.

In a preferred embodiment, the pressure sensitive adhesive is based on at least one poly(meth)acrylate (e.g. is a (meth)acrylic pressure sensitive adhesive). Poly(meth) acrylic pressure sensitive adhesives are derived from, for example, at least one alkyl (meth)acrylate ester monomer such as, for example, isooctyl acrylate, isononyl acrylate, 2-methyl-butyl acrylate, 2-ethyl-hexyl acrylate and n-butyl acrylate; and at least one optional co-monomer component such as, for example, (meth)acrylic acid, vinyl acetate, N-vinyl pyrrolidone, (meth)acrylamide, a vinyl ester, a fumarate, a polystyrene or polymethylmethacrylate macromer, or combinations thereof. Preferably, the poly (meth)acrylic pressure sensitive adhesive is derived from between about 0 and about 20 weight percent of acrylic acid and between about 100 and about 80 weight percent of at least one of isooctyl acrylate, 2-ethyl-hexyl acrylate or n-butyl acrylate composition, preferably isooctyl acrylate. A preferred embodiment for the present invention is derived from between about 2 and about 10 weight percent acrylic acid and between about 90 and about 98 weight percent of at least one of isooctyl acrylate, 2-ethyl-hexyl acrylate or n-butyl acrylate composition. One specific embodiment for the present invention is derived from about 2 weight percent to about 10 weight percent acrylic acid, about 90 weight percent to about 98 weight percent of isooctyl acrylate, and about 2 weight percent to about 6 weight percent polystyrene macromer.

Reinforcing Material

Various reinforcing materials may be used to practice the present invention. In preferred embodiments, the reinforcing material is a polymer. In specific embodiments, the reinforcing material is elastomeric. Preferably, the reinforcing material is a semi-crystalline polymer. A semi-crystalline polymer is one having both amorphous and crystalline domains. Many specific embodiments incorporate semi-crystalline polymers, such as polycaprolactone (PCL), polybutene (PB), copolymers derived from ethylene and at least one other alpha-olefin monomer (e.g. poly(ethylene-co-1-alkene) and poly(ethylene-co-1-alkene-co-1-alkene)), ultra low density polyethylene (e.g. having a density below 0.915 grams/cubic centimeter, such as ATTANE 4202 commercially available from Dow Chemical Co.), linear low density polyethylene (e.g. having a density between 0.915 and 0.94 grams/cubic centimeter, such as LL-3003, ECD-125, 377D60, 369G09, 363C32, 361C33, 357C32, 350D65, 350D64, 350D60, LL-3013, and LL-3001, EXACT 3040 commercially available from ExxonMobil Corp.) or combinations thereof.

Preferred reinforcing materials have a measurable yield strength. In certain embodiments, the yield strength of the reinforcing material is less than about 20 MPa. The tensile strength of the reinforcing material is preferably at least about 150% of its yield strength. In specific embodiments, the tensile strength of the reinforcing material is higher than the tensile strength of the pressure sensitive adhesive. These values are measured using ASTM D 882-97 at a crosshead speed of 12 inches/minute (30 centimeters/minute).

The reinforcing material preferably has a melting point above the use temperature of the adhesive composition. Similarly, the reinforcing material preferably has a melting point above the storage temperature of the adhesive composition or any article manufactured with the adhesive composition. Both the use temperature and the storage temperature should not exceed the temperature at which the pressure sensitive adhesive decomposes. In certain embodiments, the reinforcing material has a melting point of at least 70° C. All temperatures are related as being measurable by differential scanning calorimetry ("DSC") at a scanning rate of 10° C./minute.

It is particularly desirable for the reinforcing material to have a melt viscosity similar to the melt viscosity of the pressure sensitive adhesive at the processing temperature of the method of this invention. In specific embodiments, the ratio of the reinforcing material melt viscosity to the pressure sensitive adhesive melt viscosity at the processing temperature is less than about 3, preferably less than about 1.5. In particularly preferred embodiments, the ratio is between about 0.5 and about 1.2 depending on specific extrusion parameters (e.g. shear rate, screw speed, temperature). Melt viscosity is measurable as understood by one skilled in the art using a capillary viscometer.

The reinforcing material is preferably immiscible (i.e. remains in a separate phase) in the pressure sensitive adhesive during mixing so that the reinforcing material can be substantially uniformly dispersed (i.e. distributed) in the pressure sensitive adhesive. In specific embodiments, during mixing, the reinforcing material is in the form of substantially spherical particles having an average diameter less than about 20 micrometers. In certain embodiments, the reinforcing material has an average diameter less than about 10 micrometers.

In preferred embodiments, the reinforcing material exists as substantially continuous fibers in the adhesive composition. Specifically, according to one aspect of the invention, the fibers are unbroken for at least about 0.5 centimeters in the machine direction of the pressure sensitive adhesive matrix, preferably at least about 2 centimeters. In more preferred embodiments, the substantially continuous fibers are continuous for at least about 5 centimeters and most preferably at least about 8 centimeters. According to another aspect of the invention, the substantially continuous fibers generally have a maximum diameter of about 0.05 to about 5 micrometers, preferably from about 0.1 to about 1 micrometers. According to another aspect of the invention, the aspect ratio (i.e. the ratio of the length to the diameter) of the substantially continuous fibers is greater than about 1000.

In other embodiments, the reinforcing material may be useful to prevent flow or creep of the adhesive composition. In addition to the previously described materials other useful materials include polyethylene (e.g. high density polyethylene from Equistar Chemicals, Houston Tex. as well as medium-low density polyethylenes and low density polyethylenes); polypropylene copolymers; polymethyl methacrylate; thermoplastic polyurethane (TPU form Dow Chemical or BF Goodrich); polystyrene; polyvinyl acetate; polyvinyl chloride; polyoxymethylene; poly (ethylene-co-acrylic acid); poly (ethylene-co-methacrylic acid); poly (styrene-co-allyl alcohol); polyamides; polyether-co-polyamide block copolymers such as PEBAX (from Atofina Chemicals, Philadelphia, Pa.); polyesters such as TONE polymers P-767 and P-787 (from Union Carbide, Danbury, Conn.); block copolyester elastomers such as HYTREL (from DuPont, Wilmington, Del.); and mixtures thereof. Preferred materials are ATTANE 4202 (available from Dow Chemical) and EXACT 3040 (available from ExxonMobile Corp.).

Mixing

The reinforcing material is mixed with the pressure sensitive adhesive before subjecting the mixture to an elongating shear force. Mixing of the reinforcing material and the pressure sensitive adhesive is done by any method that results in a dispersion, preferably a substantially uniform dispersion, of the reinforcing material in the pressure sensitive adhesive. For example, melt blending, solvent blending, or any suitable physical means are able to adequately mix the reinforcing material and the pressure sensitive adhesive.

Melt blending devices include those that provide dispersive mixing, distributive mixing, or a combination of dispersive and distributive mixing. Both batch and continuous methods of melt blending can be used. Examples of batch methods include those using a BRABENDER (e.g. a BRABENDER PREP CENTER, commercially available from C. W. Brabender Instruments, Inc.; South Hackensack, N.J.) or BANBURY internal mixing and roll milling equipment (e.g. equipment available from Farrel Co.; Ansonia, Conn.). After batch mixing, the mixture created may be immediately quenched and stored below melting temperature of the mixture for later processing.

Examples of continuous methods include single screw extruding, twin screw extruding, disk extruding, reciprocating single screw extruding, and pin barrel single screw extruding. The continuous methods can include utilizing both distributive elements, such as cavity transfer mixers (e.g. CTM, commercially available from RAPRA Technology, Ltd.; Shrewsbury, England) and pin mixing elements, static mixing elements or dispersive mixing elements (commercially available from e.g., MADDOCK mixing elements or SAXTON mixing elements as described in "Mixing in Single-Screw Extruders," *Mixing in Polymer Processing*, edited by Chris Rauwendaal (Marcel Dekker Inc.: New York (1991), pp. 129, 176–177, and 185–186).

In certain embodiments, the reinforcing material comprises between about 2 and about 70 weight percent of the adhesive composition. In specific embodiments, the reinforcing material comprises between about 5 and about 60 weight percent of the adhesive composition. In preferred embodiments, the reinforcing material comprises between about 5 and about 50 weight percent of the adhesive composition. Typically, the pressure sensitive adhesive component comprises between about 30 and about 98 weight percent, preferably between about 40 and about 95 weight percent and more preferably between about 50 and about 95 weight percent of the total adhesive composition. Other additives may also be mixed into the pressure sensitive adhesive composition prior to application thereof, depending on the desired properties of the applied adhesive.

In some embodiments, the fibrous reinforcing material is substantially uniformly dispersed in the pressure sensitive adhesive matrix. In such an embodiment, a cross section of the adhesive composition taken perpendicular to the machine direction will reveal an array of fibers throughout the matrix with fibers present across the thickness.

Method of Forming the Fiber Reinforced Pressure Sensitive Adhesive

The adhesive composition is subjected to an elongating shear force, creating fibers from the reinforcing material in a pressure sensitive adhesive matrix. Preferably, the adhesive composition is formed by continuous forming methods, including hot melt coating, drawing or extruding, the adhesive composition from the elongating shear force device (e.g. a draw die, a film die, or a rotary rod die) and subsequently contacting the drawn adhesive composition to a moving web (e.g. plastic) or other suitable substrate. A related continuous forming method involves extruding the adhesive composition and a co-extruded backing material from a film die and cooling the layered product to form an adhesive tape. Other continuous forming methods involve directly contacting the adhesive composition to a rapidly moving web or other suitable preformed substrate. Using this method, the adhesive composition is applied to the moving preformed web using a die having flexible die lips, such as a rotary rod die.

After forming by any of these continuous methods, the fibers, thus formed, can be solidified by lowering the temperature of the adhesive composition to below the melting point of the reinforcing material. For example, the temperature may be lowered by quenching the adhesive composition using either direct methods (e.g., chill rolls or water baths) or indirect methods (e.g., air or gas impingement). The resulting fiber reinforced adhesive composition is then cooled to ambient temperature.

Application of the Fiber Reinforced Adhesive Composition

The fiber reinforced adhesive composition can be used for a variety of applications. For example, the fiber reinforced adhesive composition can be applied to sheeting products (e.g., decorative, reflective, and graphical), labelstock, and tape backings to form, for example, first aid dressings, medical drapes, or medical tapes. Additionally, the fiber reinforced adhesive composition of the present invention can be used in optical fibers and tapes. The substrate can be any suitable type of material depending on the desired application.

To form a tape, the fiber reinforced adhesive composition is coated onto at least a portion of a suitable backing. A release material (e.g., low adhesion backsize) can be applied to the opposite side of the backing, if desired. When double-coated tapes are formed, the fiber reinforced adhesive composition is coated, for example by co-extrusion or lamination, onto at least a portion of both sides of the backing. Additionally, the adhesive can be coated on at least one release liner to form a transfer tape.

Typically, the backing comprises a nonwoven, paper, polypropylene (e.g., biaxially oriented polypropylene (BOPP)), polyethylene, polyester (e.g., polyethylene terephthalate), or a release liner (e.g., siliconized liner). In specific embodiments, the backing is stretchable so that an article comprising the adhesive composition and the backing would be stretch removable.

In specific embodiments, the adhesive compositions of the present invention are used in tapes that include gauze pads, for example, and are used as first aid dressings (i.e., wound or surgical dressings). They can also be used in a wide variety of other medical articles, such as medical tapes, athletic tapes, surgical drapes, or tapes or tabs used in adhering medical devices such as sensors, electrodes (as disclosed in U.S. Pat. Nos. 5,215,087 and 6,171,985, for example), ostomy appliances, or the like.

Preferably, webs made from natural or synthetic fibers or mixtures thereof can be used to form backings, particularly for medical articles. Woven or nonwoven materials can be employed for webs, with nonwoven materials being preferred for most applications. Melt-blown or spunbond techniques can be employed to make such nonwoven webs. Nonwoven webs can also be prepared, for example, on a RANDO WEBBER (Rando Corporation, Macedon, N.Y.) air-laying machine or on a carding machine.

Typically, fibers forming a nonwoven tape backing are intimately entangled with each other in the form of a coherent breathable fibrous nonwoven tape backing. Suitable nonwoven tape backings can be formed as melt blown microfiber webs using the apparatus discussed, for example, in Wente, Van A., "Superfine Thermoplastic Fibers," *Industrial Engineering Chemistry*, Vol. 48, pages 1342–1346; Wente, Van A. et al., "Manufacture of Superfine Organic Fibers," *Report No. 4364 of the Naval Research Laboratories*, published May 25, 1954; and in U.S. Pat. Nos. 3,849,241, 3,825,379, and others. These microfine fibers are termed melt blown fibers or blown microfibers (BMF) and are generally substantially continuous and form a coherent web between the exit die orifice and a collecting surface by entanglement of the microfibers, due in part to the turbulent airstream in which the fibers are entrained.

Other conventional melt spinning type processes, such as spunbond processes, where fibers are collected in a web form immediately upon formation, can also be used to form the nonwoven tape backing. Generally, the fibers are 100 microns or less in diameter when formed by melt spinning type processes, preferably 50 microns or less.

Multicomponent fibers, if formed by the melt blown process, can be produced as described in U.S. Pat. No. 5,176,952 (Joseph et al); U.S. Pat. No. 5,232,770 (Joseph); U.S. Pat. No. 5,238,733 (Joseph et al); U.S. Pat. No. 5,258,220 (Joseph); or U.S. Pat. No. 5,248,455 (Joseph et al). Multicomponent fibers can also be produced by a spunbond process as disclosed in U.S. Pat. No. 5,695,868 (McCormach); U.S. Pat. No. 5,336,552 (Strack et al); U.S. Pat. No. 5,545,464 (Stokes); U.S. Pat. Nos. 5,382,400; 5,512,358 (Shawyer et al); or U.S. Pat. No. 5,498,463 (McDowall et al).

Representative examples of materials suitable for the backing of the adhesive article of this invention include polyolefins, such as polyethylene, including high density polyethylene, low density polyethylene, linear low density polyethylene, and linear ultra low density polyethylene, polypropylene, and polybutylenes; vinyl copolymers, such as polyvinyl chlorides, both plasticized and unplasticized, and polyvinyl acetates; olefinic copolymers, such as ethylene/methacrylate copolymers, ethylene/vinyl acetate copolymers, acrylonitrile-butadiene-styrene copolymers, and ethylene/propylene copolymers; acrylic polymers and copolymers; polycaprolactones; and combinations of the foregoing. Mixtures or blends of any plastic or plastic and elastomeric materials such as polypropylene/polyethylene, polyurethane/polyolefin, polyurethane/polycarbonate, polyurethane/polyester, can also be used. Additionally, any nonstretchable material can be used for the tearable backings or for those with perforations, including paper and even metal. Preferred materials for the backing include polyurethane, polypropylene, ethylene vinyl acetate, or combinations thereof (e.g., blends, mixtures, etc.) in the form of melt blown fibers. Preferred materials for film backings include polycaprolactones and copolymers of ethylene/vinyl acetate and linear low density polyethylene.

In a preferred embodiment, the backing is formed from coherent multicomponent fibers having at least one pressure sensitive adhesive region or layer and at least one non-pressure sensitive adhesive region or layer as described in U.S. Pat. No. 6,107,219. In another preferred embodiment, the backing is a melt blown polypropylene web available from Kimberly Clark Corp.; Irving, Tex.

If the backing is in the form of a laminate, additional components could be used, such as absorbent layers (e.g., gauze pads) for adhesive bandage products, or the like. If absorbent layers are used, they are typically thin, coherent, conformable, and able to flex and not interfere with the stretch removable characteristics of the articles, although they can be stretchable or not.

If a laminate, there may be one or more additional layers. Preferably, the outermost layer of such a laminate is a film that is substantially impervious to fluids, such as could arise from the external environment, yet permits passage of moisture vapor such that the adhesive article is breathable (typically, having a moisture vapor transmission rate (MVTR) of at least about 500 g/m$^2$/day). Typically this breathable, liquid impervious film is the outermost (i.e., top) layer. Examples of such film materials include polyurethanes, polyolefins, metallocene catalyzed polyolefins, polyesters, polyamides, polyetheresters, and A-B-A block copolymers, such as KRATON copolymers available from Shell Chemical Ltd.; Houston, Tex.

EXAMPLES

This invention is further illustrated by the following examples that are not intended to limit the scope of the invention. These examples are merely for illustrative purposes only and are not meant to be limiting on the scope of the appended claims. All parts, percentages, ratios, etc. in the examples and the rest of the specification are by weight unless indicated otherwise. All ultraviolet curing of adhesives described in the examples occurred with the adhesive directly exposed to the ultraviolet radiation source.

Table of Abbreviations

| Abbreviation/ Trade Designation | Description |
|---|---|
| AA | Acrylic acid |
| ATTANE 4202 | Ultra Low Density Linear Poly(ethylene-co-octene), commercially available from Dow Chemical Co.; Midland, MI. |
| Box Sealing Tape 311 | Box sealing tape commercially available from 3M Company; St. Paul,MN |
| Box Sealing Tape 313 | Box sealing tape commercially available from 3M Company; St. Paul, MN |
| CV-60 | A controlled viscosity grade natural rubber, available from The Goodyear Tire and Rubber Co.; Akron, OH. |
| ELVAX 210 | Ethylene-vinyl acetate copolymer commercially available from E.I. duPont deNemours and Co.; Wilmington, DE. |
| ELVAX 240 | Ethylene-vinyl acetate copolymer commercially available from E.I. duPont deNemours and Co.; Wilmington, DE. |
| ELVAX 450 | Ethylene-vinyl acetate copolymer commercially available from E.I. duPont deNemours and Co.; Wilmington, DE. |
| ELVAX 660 | Ethylene-vinyl acetate copolymer commercially available from E.I. duPont deNemours and Co.; Wilmington, DE. |
| ENGAGE 8200 | Ethylene-octene copolymer derived from 24% octene, having a DSC measured melting peak temperature of 60° C., commercially available from DuPont Dow Elastomers LLC; Wilmington, DE. |
| ENGAGE 8490 | Ethylene-octene copolymer derived from 14% octene, commercially available from DuPont Dow Elastomers LLC; Wilmington, DE. |
| ESCOREZ 2393 | Aliphatic/aromatic mixed tackifier resin commercially available from ExxonMobil Corp.; Houston, TX. |
| FINA 3376 | polypropylene commercially available from Fina Oil and Chemical Company; Dallas, Texas |
| HDPE | High Density Polyethylene, having a weight average molecular weight of 125,000 and a density of 0.95 grams/cubic centimeter, commercially available from Scientific Polymer Products, Inc.; Ontario, NY. |
| Input Film | White polypropylene film of approximately 50 micrometers (2 mils) thickness, commercially available as BW9 from Nan Ya Plastics Corp. America, Livingston, NJ |
| IOA | Isooctyl acrylate |
| IRGANOX 1010 | An antioxidant commercially available from Ciba Specialty Chemicals Corporation; Tarrytown, NY |
| KRATON D1107 | Styrene-isoprene-styrene block copolymer commercially available from Shell Chemicals Ltd.; Houston, TX. |
| LDPE | Low density polyethylene, having a density of 0.918 grams/cubic centimeter, commercially available from Aldrich Chemical Co.; Milwaukee, WI. |
| MAA | Methacrylic acid |
| PB | Isotactic Polybutene, having a weight average molecular weight of 185,000, commercially available from Aldrich Chemical Co.; Milwaukee, WI. |
| PCL | Polycaprolactone, having a weight average molecular weight of 80,000, commercially available from Aldrich Chemical Co.; Milwaukee, WI. |
| PEBH | Metallocene catalyzed poly(ethylene-co-1-butene-co-1-hexene), with a melt index of 3.5, commercially available from Aldrich Chemical Co.; Milwaukee, WI. |
| PET | An aminated-polybutadiene primed polyester film of polyethylene terephthalate having a thickness of 38 micrometers. |
| PMMA | Polymethylmethacrylate, having a weight average molecular weight of 350,000 commercially available from Aldrich Chemical Co.; Milwaukee, WI. |

-continued

Table of Abbreviations

| Abbreviation/<br>Trade Designation | Description |
|---|---|
| PP substrate | Polypropylene substrate commercially available from Aeromat Plastics Inc.; Burnsville, MN. |
| PS | Polystyrene, having a weight average molecular weight of 280,000, commercially available from Aldrich Chemical Co.; Milwaukee, WI. |
| PSA-1 | IOA/AA copolymer pressure sensitive adhesive, derived from an approximate ratio of IOA/AA monomers of 90/10. The pressure sensitive adhesive was prepared by mixing 21.6 grams of IOA, 2.4 grams of AA, 0.28 gram of carbon tetrabromide chain transfer agent, and 36 grams of ethyl acetate in a glass vessel. To this mixture, 0.072 gram of VAZO 64 was added. The vessel was made inert with nitrogen gas and sealed. The sealed bottle was tumbled in a 55° C. water bath for 24 hours. The resultant polymer was coated onto a siliconized polyester release liner and oven dried for 15 minutes at 65° C. to recover the dried polymer. |
| PSA-2 | Pressure sensitive adhesive containing a mixture of 50 parts of KRATON D1107 and 50 parts of WINGTACK PLUS. |
| PSA-3 | Kraton pressure sensitive adhesive HL-2552X, commercially available from H.B. Fuller Co.; St. Paul, MN. |
| PSA-4 | IOA/MAA copolymer pressure sensitive adhesive derived from an approximate ratio of IOA/MAA monomers of 96/4. The pressure sensitive adhesive was prepared as described in U.S. Pat. No. 4,952,650, Example 5, and dried prior to use. |
| PSA-5 | IOA/AA copolymer pressure sensitive adhesive, derived from an approximate ratio of IOA/AA monomers of 90/10. The pressure sensitive adhesive was polymerized as described in U.S. Pat. No. 5,804,610, Example 1, with the exception that the pouch was removed prior to feeding the pressure sensitive adhesive into the extruder. |
| PSA-6 | IOA/AA copolymer pressure sensitive adhesive grafted with a polystyrene macromer, derived from an approximate ratio of IOA/AA/polystyrene components of 92/4/4. The pressure sensitive adhesive was prepared as described in U.S. Pat. No. 4,554,324, Example 74, except that the macromer was polystyrene and the inherent viscosity of the resulting PSA-6 was 0.65 dl/g (measured in ethylacetate at 27° C.) |
| PSA-7 | PSA-6 mixed with 23% ESCOREZ 2393 tackifier. |
| PSA-8 | IOA/AA copolymer pressure sensitive adhesive, derived from an approximate ratio of IOA/AA monomers of 95.5/4.5 and polymerized as described in U.S. Pat. No. RE 24,906, Example 5, and dried prior to use. |
| PSA-9 | Natural rubber pressure sensitive adhesive prepared from CV-60 as described in U.S. Pat. No. 6,063,838, Examples 43–44. |
| PSA-10 | Pressure sensitive adhesive containing a mixture of 55 parts of KRATON D1107, 45 parts of WINGTACK PLUS and 1.1 parts of IRGANOX 1010. |
| REGALREZ 1126 | Hydrogenated tackifier resin commercially available from Hercules, Inc.; Wilmington, DE. |
| SCOTCHCAL 3650 | Tape commercially available from 3M Company; St. Paul, MN |
| WINGTACK PLUS | A C5 hydrocarbon tackifier resin commercially available from Goodyear Tire & Rubber Company; Akron, OH. |

Test Methods

Tensile Testing

Tensile testing was carried out according to ASTM test method D 882-97 "Standard Test Method for Tensile Properties of Thin Plastic Sheeting" using an INSTRON materials tester (commercially available from Instron; Canton, Mass.) at a crosshead speed of 30 centimeters/minute (12 inches/minute). Using this test, the values for "Yield Strength", "Tensile Strength", and "Percent Elongation at Break" were obtained.

180° Peel Adhesion

This peel adhesion test is similar to the test method described in ASTM D 3330-90, substituting a glass, high density polyethylene or polypropylene substrate for the stainless steel substrate described in the test. The substrate used is noted in each particular example.

Adhesive-coated strips that had equilibrated at constant temperature (21° C.) and humidity (50% relative humidity) for at least 24 hours, were adhered to a substrate panel using a 2 kg roller passed once over the strip. The substrate panel was either solvent-washed glass, polypropylene (PP), or high density polyethylene (HDPE). The bonded assembly was allowed to dwell at room temperature for one minute. The assembly was then tested for 180° peel adhesion in the machine direction using an IMASS slip/peel tester (Model 3M90, commercially available from Instrumentors Inc., Strongsville, Ohio) at a crosshead speed of 30 centimeters/minute (12 inches/minute).

Stretch Removable Test Method

Adhesive-coated strips, which had equilibrated at constant temperature (21° C.) and humidity (50% relative humidity) for at least 24 hours, were adhered to a polypropylene (PP) substrate panel using a 2 kilogram roller passed once over the strip. The bonded assembly was allowed to dwell at room temperature for one minute. The assembly was then tested for stretch removablity by pulling at an angle of between 15 and 35° either "by hand", or "mechanically" using an IMASS slip/peel tester (Model 3M90, commercially available from Instrumentors Inc., Strongsville, Ohio) at a crosshead speed of 30 centimeters/minute (12 inches/minute). The data are reported for the by hand samples as "broke" if the sample broke before detachment (i.e. the sample did not stretch remove), or "yes" if the sample exhibited stretch removable properties. For the mechanically tested samples, the data is reported as "broke" if the sample broke (i.e. the sample did not stretch remove), or, if the sample did exhibit stretch removable properties, the maximum stretch removable force in Newtons/decimeter is reported.

Probe Tack Test

Probe tack measurements were made following the test method described in ASTM D 2979-95 using a TA-XY2 texture tester (commercially available from Stable Microsystems, Surrey, U.K.).

Solvent Extraction Test

To determine the continuity of the fibrous reinforcing material of the adhesive composition, the pressure sensitive adhesive matrix was dissolved, leaving behind the fibrous reinforcing material. A strip of the adhesive composition film (approximately 7.5 centimeters long by 2.5 centimeters wide) was cut from the film in the machine direction. The strip was suspended on an open frame by looping the film over the edge of the open frame. The frame and adhesive strip were immersed in a solvent capable of dissolving the pressure sensitive adhesive but not the fibrous reinforcing material. After 24 hours the sample was checked to determine if the pressure sensitive adhesive had completely dissolved and if the fibrous reinforcing material remained on the frame. If fibers were not continuous for at least 5 centimeters, nothing remained on the frame. The samples were rated as "pass" if fibers remained on the frame and "fail" if no fibers remained on the frame.

Tensile Properties of Reinforcing Material

Films of possible fibrous reinforcing material were prepared by hot-press molding each reinforcing material to a thickness of 102 micrometers. The films were tested using the Tensile Testing method described above. The results are shown in Table 1. Additionally, the materials are characterized as being elastomeric (rebounds upon deformation) or plastic (deforms permanently).

TABLE 1

| Polymer | Yield Strength (MPa) | Tensile Strength (MPa) | Percent Elongation at Break (%) | Plastic or Elastomeric |
|---|---|---|---|---|
| PEBH | 5.09 | 31.72 | 730 | Elastomeric |
| PCL | 7.45 | 16.41 | 620 | Elastomeric |
| ATTANE 4202 | 8.27 | 27.58 | >800 | Elastomeric |
| HDPE | 20.55 | 14.34 | 370 | Plastic |
| PMMA | 25.51 | 25.51 | <10 | Plastic |

Preparation of Microstructured Film

The polypropylene Input Film was made into a microstructured polypropylene film by a single pass of a web of the Input Film through an extruder (extrusion coater). A fresh layer of FINA 3376 polypropylene was hot-melt coated onto the Input Film and the hot-melt layer immediately embossed while hot with a microstructured tool roll which was one of the two rolls of the extruder exit nip.

The extrusion coating and microstructure embossing were carried out using a 3.175 cm (1.25 inch) Killion Extruder. The extruder is of design that is known in the art with a heated extrusion die in close proximity to the in-running side of an extruder nip comprising two rolls closed under pressure. The molten extrudate emerged from the die and was drawn into the nip.

The extruder nip comprised two rolls of approximately 30.5 cm (12 in) in diameter; one upper rubber roll and one lower metal roll. These rolls were hollow, and could be chilled or heated by passing a fluid through the hollow interiors of the rolls. The lower metal roll was a microstructured tool roll. The cylindrical surface of the metal roll was a surface engraved with a microstructured pattern according to techniques known in the art.

The web of the polypropylene input film was wrapped through approximately 180° around the upper (rubber) roll and then passed into the nip with the freshly-extruded polypropylene melt. The microstructured surface of the tool roll embossed the extrusion-coated polypropylene layer. Thus a microstructured polypropylene film having a first major microstructured surface and a second major surface was obtained. The web was allowed to cool and wound up.

The rubber roll was maintained at a temperature of 38° C. (100° F.). The lower roll was warmed to a temperature of 110° C. (230° F.).

Best print results were obtained if the resultant microstructured film thickness was about 190 microns (7.5 mils). Therefore about 50 microns (two mils) of the microstructured film thickness is attributable to the input film and about 140 microns (5.5 mils) of the microstructured film is from the extrusion-coated polypropylene. The draw residence was adjusted so that the final film thickness was approximately 190 microns.

The web speed was between approximately 3.0 and 3.7 meters per minute (10 to 12 feet per minute).

Extruder zone temperatures were: Zone 1, 124° C. (255° F.); Zone 2, 177° C. (350° F.); Zone 3, 235° C. (455° F.); Zone 4, 243° C. (470° F.); and Zone 5, 249° C. (480° F.);

The extruder die temperature was 249° C. (480° F.).

Microstructured Tool Roll

The microstructured tool roll was a hollow metal roll approximately 30.5 cm (12 inches) in diameter. The tool was engraved with two sets of parallel grooves, the two sets being orthogonal to each other. Each set of grooves was at approximately 45° to the roll axis. These helical grooves had a depth of approximately 50 microns and a width of approximately 18 microns at the bottom and 31 microns at the top. The parallel grooves were spaced approximately 125 microns apart.

This tool roll embossed a microstructured pattern into the freshly-coated polypropylene surface. The pattern comprised wells separated by polypropylene walls. The wells were square in aspect, and the walls lay at 45° to the machine direction (web direction) of the microstructured film.

Desired microstructured patterns can be formed in tools via any number of well-known techniques, selected depending in part upon the tool material and features of the desired topography. Illustrative techniques include etching (e.g. via chemical etching, mechanical etching or other ablative means such as laser ablation or reactive ion etching, etc.), photolithography, stereolithography, micromachining, knurling (e.g. cutting, knurling or acid enhanced knurling), scoring or cutting etc. Some patents that disclose various illustrative techniques include U.S. Pat. No. 5,183,597 (Lu); U.S. Pat. No. 4,588,258 (Hoopman); and U.S. Pat. No. 5,175,030 (Lu et al.) and U.S. Pat. No. 6,285,001.

50° C. Heat Aging with Adhesion, Shear Holding and Tack Testing

In each test, a strip of microstructured adhesive tape was cut from the adhesive-coated microstructured backing. The first tape sample was applied to a second sample of the same tape (having the same adhesive), the adhesive side of the first tape sample in contact with the microstructured side of the second tape sample to give a layered construction (similar to two wraps of the tape in a roll). The layered construction of the two tape samples was pressed together at 170 kPa (25 pounds per square inch) pressure for about three days at approximately 50° C. (120° F.) and tested for 90° peel release force and behavior (pulling apart the two tape samples at an angle of 90° at a rate of 127 cm/minute (50 inches/minute), adhesion to steel (using the test method ASTM-613) and shear holding to fiberboard using the test method ASTM-1535 (all failures were by peeling off of the fiberboard unless otherwise noted).

Accelerated Adhesive Flow Test

To test an adhesive layer for adhesive flow, the following procedure was used. The test elements are a Test Sheet (in the form of a tape) and an Application Surface. The Test Sheet tape has a test sheet film (backing) and the adhesive layer to be tested coated on one side of the test sheet film. The dimensions of the Test Sheet were 11 cm by 21 cm (4.3×8.3 inches). The Application Surface used was the Microstructured Film whose preparation is described above. The dimensions of the Application Surface were 11 cm by 21 cm (4.3×8.3 inches).

The adhesive side of the Test Sheet was applied to the Application Surface using a hand held roller and gentle hand pressure to give a layered structure, in order: the test sheet film (backing); the test adhesive; the microstructured side of the Application Surface; and the Application Surface adhesive (the Application Surface used had adhesive coated onto the non-microstructrured side so that it was also a tape construction making the layered structure essentially a stacking of 2 tape samples). The test could alternatively be done with an Application Surface that does not have an adhesive layer coated on the other side.

The layered construction was pressed between two glass plates. Each glass plate was slightly larger than 21.5 cm×28 cm (8.5 inches×11 inches) and weighed approximately 630 grams. The layered construction can be sandwiched between two sheets of release liner before placing between the glass plates to avoid sticking of the layered construction to the glass. Both sheets of release liner were also approximately 21.5 cm×28 cm (8.5 inches×11 inches). The sheets of release liner are placed with the release surface in contact with the layered construction to prevent sticking of the layered construction to the glass plates. The sandwiched construction comprising the glass plates, layered construction and any release liner sheets was placed in an oven and a 1 kg weight placed on top of the glass plate sandwich for the times and temperatures shown for the individual examples.

After submitting the samples to the accelerated flow condition as described above, each layered construction was peeled apart slowly and carefully by hand.

In each sample, as expected, the microstructured surface of the adhesive backing left an impression on the test adhesive layer of the test sheet. These impressions were examined by optical microscope (a Leica DMLM Optical Microsystems microscope, available from Leica Microsystems; Deerfield, Ill.).

The microscope was focused on the bottoms of the microstructured grooves in the adhesive structure and the microscope focus adjustment height read. Without altering the sample position in any way, the microscope was refocused on the square plateau regions of adhesive between the grooves. The microscope focus adjustment height was again read, and the difference calculated. This difference is the height of top of the square features (the plateaus) above the bottoms of the grooves. This is the distance the adhesive flowed into the microstructure during the 70° C. flow test. The greater this distance, the higher the flow of the adhesive during the test. Conversely, the lower this distance, the lower the flow of the adhesive during the test. Results are listed as the distance (in micrometers) of flow for the given test conditions.

Steady State Shear Creep

The creep compliance and low deformation rate viscosity characteristics of various adhesives were evaluated. More specifically, the adhesive material was subjected to a constant load (stress). The resulting deformation (strain) was measured as a function of time. The shear creep test was run on a Universal Stress Rheometer (Model SR5, available from Rheometric Scientific, Piscataway, N.J.). Test samples of the adhesive were prepared by coating the material onto a release liner, drying it, and folding the resulting adhesive film back on itself to create a thin adhesive slab having a thickness of about 0.039 to 0.079 inches (1 to 2 mm). A 1 inch (25 mm) diameter sample of the adhesive was cut from the slab and mounted between the parallel plates of the rheometer. The creep test was performed at a constant temperature of 158° F. (70° C.) with a constant stress of 10,000 Pascals applied to the sample for a time of 1300 seconds. After 1300 seconds, the constant stress was removed and the decay in strain was measured. The steady state compliance (Jo) and the low deformation rate viscosity ($\eta_o$) were calculated from the results as follows.

The strain ($\gamma$) was measured as a function of time and the compliance (J) calculated therefrom using Equation 1:

$$J(t) = \gamma(t)/\sigma \quad (1)$$

where J is compliance, $\gamma$ strain, t is time and $\sigma$ is stress.

The steady state compliance ($J_0$) and low deformation rate viscosity ($\eta_0$) were calculated from a plot of compliance versus time using Equation 2:

$$J(t) = (1/\eta_0)t + J_0 \quad (2)$$

where J is compliance, t is time, ($1/\eta_0$) represents the slopeline in the steady state region of the compliance curve, and $J_0$ is compliance at time zero as determined by the y intercept of the slopeline.

Comparative Example C1

A sample of PSA-1 was hot melt coated between two release liners at 150° C. using a HAAKE single screw extruder (commercially available from Haake, Inc.; Paramus, N.J.) equipped with a draw die. The resulting film had a thickness of 127 micrometers. The tensile properties of the film were determined as described in the Tensile Testing method above. The results are shown in Table 2. A portion of the film was laminated to a PET backing to make a tape. The resulting tape was passed below a Fusion H-bulb lamp (commercially available from Fusion Total Ultraviolet Systems, Inc.; Gaithersburg, Md.) at a crosshead speed of 15 meters/minute for a total ultraviolet dose of 300 milliJoules/cm². The tape was tested for 180° Peel Adhesion from glass. The results are shown in Table 3.

Example 1

A mixture of 90 parts PSA-1, 10 parts ENGAGE 8200 and 0.2 part benzophenone was prepared in a BRABENDER mixer (commercially available from C. W. Brabender Instruments, South Hackensack, N.J.) at 140° C. to 150° C. for 8 to 10 minutes. The resulting mixture was hot melt coated between two release liners at 150° C. using a HAAKE single screw extruder (commercially available from Haake, Inc.; Paramus, N.J.) equipped with a draw die. The resulting film had a thickness of 127 micrometers. The tensile properties of the film were determined as described in the Tensile Testing method above. The results are shown in Table 2. A portion of the film was laminated to a PET backing to make a tape. The resulting tape was passed below a Fusion H-bulb lamp (commercially available from Fusion Total Ultraviolet Systems, Inc.; Gaithersburg, Md.) at a crosshead speed of 15 meters/minute for a total ultraviolet dose of 300 milliJoules/cm². The tape was tested for 180° Peel Adhesion from glass. The results are shown in Table 3.

Example 2

A mixture of 90 parts PSA-1, 10 parts of LDPE and 0.2 part benzophenone were mixed in a BRABENDER mixer (commercially available from C. W. Brabender Instruments, South Hackensack, N.J.) at 140° C. to 150° C. for 8 to 10 minutes. The resulting mixture was hot melt coated between two release liners at 150° C. using a HAAKE single screw extruder (commercially available from Haake, Inc.; Paramus, N.J.) equipped with a draw die. The resulting film had a thickness of 127 micrometers. The tensile properties of the film were determined as described in the Tensile Testing method above. The results are shown in Table 2. A portion of the film was laminated to a PET backing to make a tape. The resulting tape was passed below a Fusion H-bulb lamp (commercially available from Fusion Total Ultraviolet Systems, Inc.; Gaithersburg, Md.) at a crosshead speed of 15 meters/minute for a total ultraviolet dose of 300 milliJoules/cm². The tape was tested for 180° Peel Adhesion from glass. The results are shown in Table 3.

Example 3

A mixture of 90 parts PSA-1, 10 parts ENGAGE 8490 and 0.2 part benzophenone were mixed in a BRABENDER mixer (commercially available from C. W. Brabender Instruments, South Hackensack, N.J.) at 140° C. to 150° C. for 8 to 10 minutes. The resulting mixture was hot melt coated between two release liners at 150° C. using a HAAKE single screw extruder (commercially available from Haake, Inc.; Paramus, N.J.) equipped with a draw die. The resulting film had a thickness of 127 micrometers. The tensile properties of the film were determined as described in the Tensile Testing method above. The results are shown in Table 2. A portion of the film was laminated to a PET backing to make a tape. The resulting tape was passed below a Fusion H-bulb lamp (commercially available from Fusion Total Ultraviolet Systems, Inc.; Gaithersburg, Md.) at a crosshead speed of 15 meters/minute for a UV dose of 300 milliJoules/cm$^2$. The tape was tested for 180° Peel Adhesion from glass. The results are shown in Table 3.

Example 4

A mixture of 90 parts PSA-1, 10 parts of ATTANE 4202 and 0.2 part benzophenone were mixed in a BRABENDER mixer (commercially available from C. W. Brabender Instruments, South Hackensack, N.J.) at 140° C. to 150° C. for 8 to 10 minutes. The resulting mixture was hot melt coated between two release liners at 150° C. using a HAAKE single screw extruder (commercially available from Haake, Inc.; Paramus, N.J.) equipped with a draw die. The resulting film had a thickness of 127 micrometers. The tensile properties of the film were determined as described in the Tensile Test Method above. The results are shown in Table 2. A portion of the film was laminated to a PET backing to make a tape. The resulting tape was passed below a Fusion H-bulb lamp (commercially available from Fusion Total Ultraviolet Systems, Inc.; Gaithersburg, Md.) at a crosshead speed of 15 meters/minute for a UV dose of 300 milliJoules/cm$^2$. The tape was tested for 180° Peel Adhesion from glass. The results are shown in Table 3.

TABLE 2

| Example | Yield Strength (MegaPascals) | Tensile Strength (MegaPascals) | Percent Elongation at Break (%) |
| --- | --- | --- | --- |
| C1 | 0.04 | 0.06 | >800 |
| 1 | 0.18 | 0.65 | >800 |
| 2 | 1.19 | 1.59 | 320 |
| 3 | 0.33 | 1.70 | 760 |
| 4 | 0.54 | 2.05 | 700 |

TABLE 3

| Example | 180° Peel Adhesion (N/dm) |
| --- | --- |
| C1 | 57.8 |
| 1 | 52.1 |
| 2 | 61.9 |
| 3 | 95.0 |
| 4 | 88.4 |

Comparative Example C2

A sample of PSA-1 was hot melt coated between two release liners at 150° C. using a HAAKE single screw extruder (commercially available from Haake, Inc.; Paramus, N.J.) equipped with a draw die. The resulting film had a thickness of 127 micrometers and was laminated to a PET backing to make a tape. The resulting tape was passed below a Fusion H-bulb lamp (commercially available from Fusion Total Ultraviolet Systems, Inc.; Gaithersburg, Md.) at a crosshead speed of 15 meters/minute for a UV dose of 300 milliJoules/cm$^2$. The tape was tested for 180° Peel Adhesion from glass in the machine and the cross-web directions. The results are shown in Table 4.

Example 5

A mixture of 90 parts PSA-1 and 10 parts of ATTANE 4202 were mixed in a BRABENDER mixer (commercially available from C. W. Brabender Instruments, South Hackensack, N.J.) at 140° C. to 150° C. for 8 to 10 minutes. The resulting mixture was hot melt coated between two release liners at 150° C. using a HAAKE single screw extruder (commercially available from Haake, Inc.; Paramus, N.J.) equipped with a draw die. The resulting film had a thickness of 127 micrometers and was laminated to a PET backing to make a tape. The resulting tape was passed below a Fusion H-bulb lamp (commercially available from Fusion Total Ultraviolet Systems, Inc.; Gaithersburg, Md.) at a crosshead speed of 15 meters/minute for a UV dose of 300 milliJoules/cm$^2$. The tape was tested for 180° Peel Adhesion from glass in the machine and the cross-web directions. The results are shown in Table 4.

TABLE 4

| Example | 180° Peel Adhesion in Machine Direction (N/dm) | 180° Peel Adhesion in Cross-web Direction (N/dm) |
| --- | --- | --- |
| C2 | 81.4 | 65.9 |
| 5 | 128.9 | 141.3 |

Comparative Example C3

A sample of PSA-1 was hot melt coated between two release liners at 150° C. using a HAAKE single screw extruder (commercially available from Haake, Inc.; Paramus, N.J.) equipped with a draw die. The resulting film had a thickness of 51 micrometers and was laminated to a PET backing to make a tape. The resulting tape was passed below a Fusion H-bulb lamp (commercially available from Fusion Total Ultraviolet Systems, Inc.; Gaithersburg, Md.) at a crosshead speed of 15 meters/minute for a UV dose of 300 milliJoules/cm$^2$. The tape was tested for 180° Peel Adhesion from glass in the machine and cross-web directions. The results are shown in Table 5.

Example 6

A mixture of 90 parts PSA-1 and 10 parts of LDPE were mixed in a BRABENDER mixer (commercially available from C. W. Brabender Instruments, South Hackensack, N.J.) at 140° C. to 150° C. for 8 to 10 minutes. The resulting mixture was hot melt coated between two release liners at 150° C. using a HAAKE single screw extruder (commercially available from Haake, Inc.; Paramus, N.J.) equipped with a draw die. The resulting film had a thickness of 51 micrometers and was laminated to a PET backing to make a tape. The tape was tested for 180° Peel Adhesion from glass in the machine and cross-web directions. The results are shown in Table 5.

Example 7

A mixture of 90 parts PSA-1 and 10 parts of ATTANE 4202 were mixed in a BRABENDER mixer (commercially available from C. W. Brabender Instruments, South Hackensack, N.J.) at 140° C. to 150° C. for 8 to 10 minutes. The resulting mixture was hot melt coated between two release liners at 150° C. using a HAAKE single screw extruder (commercially available from Haake, Inc.; Paramus, N.J.) equipped with a draw die. The resulting film had a thickness of 51 micrometers and was laminated to a PET backing to make a tape. The resulting tape was passed below a Fusion H-bulb lamp (commercially available from Fusion Total Ultraviolet Systems, Inc.; Gaithersburg, Md.) at a crosshead speed of 15 meters/minute for a UV dose of 300 milliJoules/cm$^2$. The tape was tested for 180° Peel Adhesion from glass in the machine and cross-web directions. The results are shown in Table 5.

TABLE 5

| Example | 180° Peel Adhesion in Machine Direction (N/dm) | 180° Peel Adhesion in Cross-web Direction (N/dm) |
|---|---|---|
| C3 | 54.9 | 51.4 |
| 6 | 36.7 | 63.0 |
| 7 | 96.9 | 88.4 |

Comparative Example C4

A sample of PSA-2 was hot melt coated between two release liners at 150° C. using a HAAKE single screw extruder (commercially available from Haake, Inc.; Paramus, N.J.) equipped with a draw die. The resulting film had a thickness of 127 micrometers and was laminated to a PET backing to make a tape. The tape was tested for 180° Peel Adhesion on various substrates. The results are shown in Table 6.

Example 8

A mixture of 90 parts PSA-2 and 10 parts of ATTANE 4202 were mixed in a BRABENDER mixer (commercially available from C. W. Brabender Instruments, South Hackensack, N.J.) at 140° C. to 150° C. for 8 to 10 minutes. The resulting mixture was hot melt coated between two release liners at 150° C. using a HAAKE single screw extruder (commercially available from Haake, Inc.; Paramus, N.J.) equipped with a draw die. The resulting film had a thickness of 127 micrometers and was laminated to a PET backing to make a tape. The tape was tested for 180° Peel Adhesion on various substrates. The results are shown in Table 6.

TABLE 6

| Example | 180° Peel Adhesion from glass (N/dm) | 180° Peel Adhesion for HDPE (N/dm | 180° Peel Adhesion from PP (N/dm) |
|---|---|---|---|
| C4 | 181 | 79 | 156 |
| 8 | 238 | 91 | 231 |

Comparative Example C5

A sample of PSA-3 was used as obtained and hot melt coated between two release liners at 150° C. using a HAAKE single screw extruder (commercially available from Haake, Inc.; Paramus, N.J.) equipped with a draw die. The resulting film had a thickness of 127 micrometers and was laminated to a PET backing to make a tape. The tape was tested for 180° Peel Adhesion on various substrates. The results are shown in Table 7.

Example 9

A mixture of 90 parts PSA-3 and 10 parts of ATTANE 4202 were mixed in a BRABENDER mixer (commercially available from C. W. Brabender Instruments, South Hackensack, N.J.) at 140° C. to 150° C. for 8 to 10 minutes. The resulting mixture was hot melt coated between two release liners at 150° C. using a HAAKE single screw extruder (commercially available from Haake, Inc.; Paramus, N.J.) equipped with a draw die. The resulting film had a thickness of 127 micrometers and was laminated to a PET backing to make a tape. The tape was tested for 180° Peel Adhesion on various substrates. The results are shown in Table 7.

TABLE 7

| Example | 180° Peel Adhesion from glass (N/dm) | 180° Peel Adhesion from HDPE (N/dm) | 180° Peel Adhesion from PP (N/dm) |
|---|---|---|---|
| C5 | 53 | 25 | 33 |
| 9 | 100 | 23 | 42 |

Comparative Example C6

A sample of PSA-4 was hot melt coated between two release liners at 150° C. using a HAAKE single screw extruder (commercially available from Haake, Inc.; Paramus, N.J.) equipped with a draw die. The tensile properties of the film were determined as described in the Tensile Testing method above. The results are shown in Table 8.

Example 10

A mixture of 85 parts PSA-4 and 15 parts of PS were mixed in a BRABENDER mixer (commercially available from C. W. Brabender Instruments, South Hackensack, N.J.) at 140° C. to 150° C. for 8 to 10 minutes. The resulting mixture was hot melt coated between two release liners at 150° C. using a HAAKE single screw extruder (commercially available from Haake, Inc.; Paramus, N.J.) equipped with a draw die. The tensile properties of the film were determined as described in the Tensile Testing method above. The results are shown in Table 8.

Example 11

A mixture of 85 parts PSA-4 and 15 parts HDPE were mixed in a BRABENDER mixer (commercially available from C. W. Brabender Instruments, South Hackensack, N.J.) at 140° C. to 150° C. for 8 to 10 minutes. The resulting mixture was hot melt coated between two release liners at 150° C. using a HAAKE single screw extruder (commercially available from Haake, Inc.; Paramus, N.J.) equipped with a draw die. The tensile properties of the film were determined as described in the Tensile Testing method above. The results are shown in Table 8.

Example 12

A mixture of 85 parts PSA-4 and 15 parts of ATTANE 4202 were mixed in a BRABENDER mixer (commercially available from C. W. Brabender Instruments, South Hackensack, N.J.) at 140° C. to 150° C. for 8 to 10 minutes. The resulting mixture was hot melt coated between two release liners at 150° C. using a HAAKE single screw extruder (commercially available from Haake, Inc.; Paramus, N.J.) equipped with a draw die. The tensile properties of the film were determined as described in the Tensile Testing method above. The results are shown in Table 8.

Example 13

A mixture of 85 parts PSA-4 and 15 parts PEBH were mixed in a BRABENDER mixer (commercially available from C. W. Brabender Instruments, South Hackensack, N.J.) at 140° C. to 150° C. for 8 to 10 minutes. The resulting mixture was hot melt coated between two at 150° C. using a HAAKE single screw extruder (commercially available from Haake,Inc.; Paramus, N.J.) equipped with a draw die. The tensile properties of the film were determined as described in the Tensile Testing method above. The results are shown in Table 8.

TABLE 8

| Example | Yield Strength (MegaPascals) | Tensile Strength (megaPascals) | Percent Elongation at Break (%) |
|---|---|---|---|
| C6 | 0.03 | 0.14 | >800 |
| 10 | 1.79 | 1.79 | <50 |
| 11 | 1.72 | 2.07 | 180 |
| 12 | 1.21 | 3.38 | >800 |
| 13 | 0.47 | 2.83 | 630 |

Examples 14–18

Mixtures for Examples 14–18 were prepared using PSA-5 with the level of ATTANE 4202 shown in Table 9, were mixed in a BRABENDER mixer (commercially available from C. W. Brabender Instruments, South Hackensack, N.J.) at 140° C. to 150° C. for 8 to 10 minutes. The resulting mixture was hot melt coated between two release liners at 150° C. using a HAAKE single screw extruder (commercially available from Haake, Inc.; Paramus, N.J.) equipped with a draw die. The tensile properties of the films were determined as described in the Tensile Testing method above. The results are shown in Table 9.

TABLE 9

| Example | Level of ATTANE 4202 (weight %) | Yield Strength (MegaPascals) | Tensile Strength (MegaPascals) | Percent Elongation at Break (%) |
|---|---|---|---|---|
| 14 | 5 | 0.21 | 0.90 | 610 |
| 15 | 10 | 0.52 | 1.79 | 670 |
| 16 | 15 | 0.95 | 3.59 | 610 |
| 17 | 30 | 2.21 | 7.31 | 650 |
| 18 | 40 | 3.45 | 13.51 | 580 |

Example 19–24

The mixtures for Examples 19–24 were prepared using PSA-4 with 15 weight % of a polymer as shown in Table 10, and were mixed in a BRABENDER mixer (commercially available form C. W. Brabender Instruments, South Hackensack, N.J.) at 140° C. to 150° C. for 8 to 10 minutes. The resulting mixture was hot melt coated between two release liners at 150° C. using a HAAKE single screw extruder (commercially available from Haake, Inc.; Paramus, N.J.) equipped with a draw die to give a thickness of 51 micrometers. The stretch removable properties of the films were determined as described in the Stretch Removable Test Method above. The results are shown in Table 10.

TABLE 10

| Example | Polymer Added (15 weight %) | Stretch removable "by hand" |
|---|---|---|
| 19 | PMMA | Broke |
| 20 | PS | Broke |
| 21 | HDPE | Broke |
| 22 | ATTANE 4202 | Yes |
| 23 | PEBH | Yes |
| 24 | PB | Yes |

Examples 25–30 and Comparative Example C7

The mixtures for Examples 25–30 and Comparative Example C7 were prepared using PSA-4 with the level of ATTANE 4202 shown in Table 11, and were mixed in a BRABENDER mixer (commercially available from C. W. Brabender Instruments, South Hackensack, N.J.) at 140° C. to 150° C. for 8 to 10 minutes. The resulting mixture was hot melt coated between two release liners at 150° C. using a HAAKE single screw extruder (commercially available from Haake, Inc.; Paramus, N.J.) equipped with a draw die to give a thickness of 51 micrometers. The stretch removable properties of the films were determined as described in the Stretch Removable Test Method above. The results are shown in Table 11.

TABLE 11

| Example | Level of ATTANE 4202 (weight %) | Stretch removable Force (N/dm) |
|---|---|---|
| C7 | 0 | Broke |
| 25 | 5 | 7.4 |
| 26 | 10 | 10.7 |
| 27 | 15 | 13.1 |
| 28 | 20 | 14.1 |
| 29 | 30 | 19.6 |
| 30 | 40 | 22.1 |

Examples 31–33 and Comparative Example C8

The mixtures for Examples 31–33 and Comparative Example C8 were prepared using PSA-6 with the level of ATTANE 4202 shown in Table 12 mixed in a BRABENDER mixer (commercially available from C. W. Brabender Instruments, South Hackensack, N.J.) at 140° C. to 150° C. for 8 to 10 minutes. The resulting mixture was hot melt coated between two release liners at 150° C. using a HAAKE single screw extruder (commercially available from Haake, Inc.; Paramus, N.J.) equipped with a draw die to give a thickness of 51 micrometers. The stretch removable properties of the films were determined as described in the Stretch Removable Test Method above. The results are shown in Table 12.

TABLE 12

| Example | Level of ATTANE 4202 (weight %) | Stretch removable Force (N/dm) |
|---|---|---|
| C8 | 0 | Broke |
| 31 | 5 | 9.0 |
| 32 | 10 | 10.3 |
| 33 | 20 | 14.3 |

Examples 34–35 and Comparative Example C9

The mixtures for Examples 34–35 and Comparative Example C9 were prepared using PSA-7 with the level of ATTANE 4202 shown in Table 13 mixed in a BRABENDER mixer (commercially available from C. W. Brabender Instruments, South Hackensack, N.J.) at 140° C. to 150° C. for 8 to 10 minutes. The resulting mixture was hot melt coated between two release liners at 150° C. using HAAKE single screw extruder (commercially available from Haake, Inc.; Paramus, N.J.) equipped with a draw die to give a thickness of 127 micrometers. The stretch removable properties of the films were determined as described in the Stretch Removable Test Method above. The results are shown in Table 13.

TABLE 13

| Example | Level of ATTANE 4202 (weight %) | Stretch Removable Force (N/dm) |
|---|---|---|
| C9 | 0 | Broke |
| 34 | 10 | 9.0 |
| 35 | 20 | 19.8 |

Examples 36–38 and Comparative Example C10

The mixtures for Examples 36–38 and Comparative Example C10 were prepared using PSA-6 with the level of ATTANE 4202 shown in Table 14 mixed in a BRABENDER mixer (commercially available from C. W. Brabender Instruments, South Hackensack, N.J.) at 140° C. to 150° C. for 8 to 10 minutes. The resulting mixture was hot melt coated between two release liners at 150° C. using a HAAKE single screw extruder (commercially available from Haake, Inc.; Paramus, N.J.) equipped with a draw die to give a thickness of 51 micrometers. The probe tack properties of the films were determined as described in the Probe Tack Test method above. The results are shown in Table 14.

TABLE 14

| Example | Level of ATTANE 4202 (weight %) | Probe Tack for 51 micrometer thick sample (grams) |
|---|---|---|
| C10 | 0 | 261 |
| 36 | 5 | 262 |
| 37 | 10 | 229 |
| 38 | 20 | 279 |

Examples 39–40 and Comparative Example C11

The mixtures for Examples 39–40 and Comparative Example C11 were prepared using PSA-7 with the level of ATTANE 4202 shown in Table 15 mixed in a BRABENDER mixer (commercially available from C. W. Brabender Instruments, South Hackensack, N.J.) at 140° C. to 150° C. for 8 to 10 minutes. The resulting mixture was hot melt coated between two release liners at 150° C. using a HAAKE single screw extruder (commercially available from Haake, Inc.; Paramus, N.J.) equipped with a draw die to give a thickness of 51 or 127 micrometers. The probe tack properties of the films were determined as described in the Probe Tack Test method above. The results are shown in Table 15.

TABLE 15

| Example | Level of ATTANE 4202 (weight %) | Probe Tack for 127 micrometer thick sample (grams) | Probe Tack for 51 micrometer thick sample (grams) |
|---|---|---|---|
| C11 | 0 | 442 | 376 |
| 39 | 10 | 340 | 328 |
| 40 | 20 | 384 | 316 |

Examples 41–45 and Comparative Example C12

The mixtures for Examples 41–45 and Comparative Example C12 were prepared using PSA-4 with the level of ATTANE 4202 shown in Table 16 mixed in a BRABENDER mixer (commercially available from C. W. Brabender Instruments, South Hackensack, N.J.) at 140° C. to 150° C. for 8 to 10 minutes. The resulting mixtures were hot melt coated between two release liners at 150° C. using a HAAKE single screw extruder (commercially available from Haake, Inc.; Paramus, N.J.) equipped with a draw die to give films having a thickness of 51 or 127 micrometers. The probe tack properties of the films were determined as described in the Probe Tack Test method above. The results are shown in Table 16.

TABLE 16

| Example | Level of ATTANE 4202 (weight %) | Probe Tack for 127 micrometer thick sample (grams) | Probe Tack for 51 micrometer thick sample (grams) |
|---|---|---|---|
| C12 | 0 | 249 | 160 |
| 41 | 5 | 261 | 197 |
| 42 | 10 | 276 | 119 |
| 43 | 15 | 157 | 156 |
| 44 | 20 | 113 | 103 |
| 45 | 30 | 87 | 73 |

Comparative Examples C13–C14

Mixtures of PSA-8 and ELVAX 240 were prepared with the levels of ELVAX 240 shown in Table 17 and hot melt coated to form films as described in U.S. Pat. No. 6,063,838 (Patnode, et al) Examples 1–17. The tensile properties of the films were determined as described in the Tensile Testing method above. The results are shown in Table 17.

TABLE 17

| Example | Level of ELVAX 240 (weight %) | Yield Strength (MegaPascals) | Tensile Strength (MegaPascals) | Percent Elongation at Break (%) |
|---|---|---|---|---|
| C13 | 10 | 1.01 | 1.10 | 408 |
| C14 | 15 | 1.43 | 1.52 | 460 |

Comparative Examples C15–C16

Mixtures of PSA-8 and ELVAX 210 were prepared with the levels of ELVAX 210 shown in Table 18 and hot melt coated to form films as described in U.S. Pat. No. 6,063,838 (Patnode, et al) Examples 1–17. The tensile properties of the films were determined as described in the Tensile Testing method above. The results are shown in Table 18.

TABLE 18

| Example | Level of ELVAX 210 (weight %) | Yield Strength (MegaPascals) | Tensile Strength (MegaPascals) | Percent Elongation at Break (%) |
|---|---|---|---|---|
| C15 | 10 | 1.38 | 1.42 | 470 |
| C16 | 15 | 1.45 | 1.52 | 460 |

Comparative Examples C17–C18

Mixtures of PSA-9 and ELVAX 240 were prepared with the levels of ELVAX 240 shown in Table 19 and hot melt coated to form films as described in U.S. Pat. No. 6,063,838 (Patnode, et al) Examples 43–44. The tensile properties of the films were determined as described in the Tensile Testing method above. The results are shown in Table 19.

TABLE 19

| Example | Level of ELVAX 240 (weight %) | Yield Strength (MegaPascals) | Tensile Strength (MegaPascals) | Percent Elongation at Break (%) |
|---|---|---|---|---|
| C17 | 10 | 0.33 | 0.37 | 270 |
| C18 | 15 | 0.32 | 0.36 | 120 |

Comparative Examples C19–C20

Mixtures of PSA-9 and ELVAX 210 were prepared with the levels of ELVAX 210 shown in Table 20 and hot melt coated to form films as described in U.S. Pat. No. 6,063,838 (Patnode, et al) Examples 43–44. The tensile properties of the films were determined as described in the Tensile Testing method above. The results are shown in Table 20.

TABLE 20

| Example | Level of ELVAX 240 (weight %) | Yield Strength (MegaPascals) | Tensile Strength (MegaPascals) | Percent Elongation at Break (%) |
|---|---|---|---|---|
| C19 | 10 | 0.07 | 0.08 | 160 |
| C20 | 15 | 0.14 | 0.16 | 220 |

Comparative Examples C21–C22

Mixtures of PSA-8 and ELVAX 450 were prepared with the levels of ELVAX 450 shown in Table 21 and hot melt coated to form films as described in U.S. Pat. No. 6,063,838 (Patnode, et al) Examples 1–17. The tensile properties of the films were determined as described in the Tensile Testing method above. The results are shown in Table 21.

TABLE 21

| Example | Level of ELVAX 450 (weight %) | Yield Strength (MegaPascals) | Tensile Strength (MegaPascals) | Percent Elongation at Break (%) |
|---|---|---|---|---|
| C21 | 10 | 1.65 | 1.72 | 260 |
| C22 | 15 | 2.55 | 2.69 | 270 |

Comparative Examples C23–C24

Mixtures of PSA-8 and ELVAX 660 were prepared with the levels of ELVAX 660 shown in Table 22 and hot melt coated to form films as described in U.S. Pat. No. 6,063,838 (Patnode, et al) Examples 1–17. The tensile properties of the films were determined as described in the Tensile Testing method above. The results are shown in Table 22.

TABLE 22

| Example | Level of ELVAX 660 (weight %) | Yield Strength (MegaPascals) | Tensile Strength (MegaPascals) | Percent Elongation at Break (%) |
|---|---|---|---|---|
| C23 | 10 | 2.41 | 2.48 | 220 |
| C24 | 15 | 2.14 | 2.21 | 240 |

Examples 46–49

The mixtures for Examples 46–49 were prepared using PSA-5 with the level of ATTANE 4202 shown in Table 23, and were mixed in a BRABENDER mixer (commercially available from C. W. Brabender Instruments, South Hackensack, N.J.) at 140° C. to 150° C. for 8 to 10 minutes. The resulting mixture was hot melt coated between two release liners at 150° C. using a HAAKE single screw extruder (commercially available from Haake, Inc.; Paramus, N.J.) equipped with a draw die. The solvent extraction properties of the film were determined as described in the Solvent Extraction Test method above. The results are shown in Table 23.

TABLE 23

| Example | Level of ATTANE 4202 (weight %) | Solvent Extraction Test Result |
|---|---|---|
| 46 | 10 | Pass |
| 47 | 15 | Pass |
| 48 | 30 | Pass |
| 49 | 40 | Pass |

Comparative Examples C25–C26

Mixtures of PSA-8, with ELVAX 210 were prepared with the levels of ELVAX 210 shown in Table 24 and hot melt coated to form films as described in U.S. Pat. No. 6,063,838 (Patnode, et al) Examples 1–17. The solvent extraction properties of the films were determined as described in the Solvent Extraction Test method above. The results are shown in Table 24.

TABLE 24

| Example | Level of ELVAX 210 (weight %) | Solvent Extraction Test Result |
|---|---|---|
| C25 | 10 | Fail |
| C26 | 15 | Fail |

Comparative Examples C27–C28

Mixtures of PSA-8 and ELVAX 240 were prepared with the levels of ELVAX 240 shown in Table 25 and hot melt coated to form films as described in U.S. Pat. No. 6,063,838 (Patnode, et al) Examples 1–17. The solvent extraction properties of the films were determined as described in the Solvent Extraction Test method above. The results are shown in Table 25.

TABLE 25

| Example | Level of ELVAX 240 (weight %) | Solvent Extraction Test Result |
|---|---|---|
| C27 | 10 | Fail |
| C28 | 15 | Fail |

Comparative Examples C29–C30

Mixtures of PSA-9 and ELVAX 210 were prepared with the levels of ELVAX 210 shown in Table 26 and hot melt coated to form films as described in U.S. Pat. No. 6,063,838 (Patnode, et al) Examples 43–44. The solvent extraction properties of the films were determined as described in the Solvent Extraction Test method above. The results are shown in Table 26.

TABLE 26

| Example | Level of ELVAX 210 (weight %) | Solvent Extraction Test Result |
|---|---|---|
| C29 | 10 | Fail |
| C30 | 15 | Fail |

Comparative Examples C31–C32

Mixtures of PSA-9 and ELVAX 240 were prepared with the levels of ELVAX 240 shown in Table 27 and hot melt coated to form films as described in U.S. Pat. No. 6,063,838 (Patnode, et al) Examples 43–44. The solvent extraction properties of the films were determined as described in the Solvent Extraction Test method above. The results are shown in Table 27.

TABLE 27

| Example | Level of ELVAX 240 (weight %) | Solvent Extraction Test Result |
|---|---|---|
| C31 | 10 | Fail |
| C32 | 15 | Fail |

Comparative Examples C33–C34

Mixtures of PSA-8 and ELVAX 450 were prepared with the levels of ELVAX 450 shown in Table 28 and hot melt coated to form films as described in U.S. Pat. No. 6,063,838 (Patnode, et al) Examples 1–17. The solvent extraction properties of the films were determined as described in the Solvent Extraction Test method above. The results are shown in Table 28.

TABLE 28

| Example | Level of ELVAX 450 (weight %) | Solvent Extraction Test Result |
|---|---|---|
| C33 | 10 | Fail |
| C34 | 15 | Fail |

Comparative Examples C35–C36

Mixtures of PSA-8 and ELVAX 660 were prepared with the levels of ELVAX 660 shown in Table 29 and hot melt coated to form films as described in U.S. Pat. No. 6,063,838 (Patnode, et al) Examples 1–17. The solvent extraction properties of the films were determined as described in the Solvent Extraction Test method above. The results are shown in Table 29.

TABLE 29

| Example | Level of ELVAX 660 (weight %) | Solvent Extraction Test Result |
|---|---|---|
| C35 | 10 | Fail |
| C36 | 15 | Fail |

Example 50

A stretch removable First Aid Dressing (FAD) sample was made by laminating with thumb pressure at room temperature a strip (2.54-cm×7.6-cm) of a perforated polymer film backing to a strip (2.54-cm×7.6-cm) of the adhesive described in Example 20, with the fibers perpendicular to the long axis of the sample. The film backing comprised 60% ethylene/vinyl acetate copolymer, 35% linear low density polyethylene, 5% stabilizers and other additives (PGI Product No. 6012, Polymer Group, Inc., Gainesville, Ga.); and the film had a basis weight of 1.15 oz/yd$^2$ (27 g/m$^2$), was 5-mils (0.13-mm) thick, and had oval-shaped holes (approximately 0.2-mm width×0.3-mm length in the greatest dimensions) with the length dimension of the oval holes oriented parallel to the machine direction of the film. The film had about 530 holes/cm$^2$ arranged in a pattern of staggered lines.

The FAD sample was evaluated for ease of removal by adhering the sample with finger pressure to the forearm of a human subject, waiting 60 minutes, and then removing by pulling one end of the sample and stretching the sample at about a 35° angle to the plane of the forearm. Very little force was required to stretch the backing and to remove the sample painlessly from the skin and hair of the forearm.

Example 51

A polyurethane backing (melt-blown nonwoven fibrous web comprised of three-layer polymeric fibers having a center layer of blended polyethylene and Kraton™ PSA, and outer layers of polyurethane; prepared as described for Backing Sample 16 in U.S. Pat. No. 6,107,219 (Joseph et al.)) was perforated with a metal die to provide parallel rows of holes separated by 3.8 cm. The holes were rectangular in shape (1.75-mm×0.07-mm) and the space between holes within a row was 0.7 mm. The polyurethane backing had one side rougher than the other due to the collection technique used during the melt-blown process.

A stretch removable FAD sample was made by laminating with thumb pressure at room temperature a strip (2.54-cm×7.6-cm) of the perforated polyurethane backing to a strip (2.54-cm×7.6-cm) of the adhesive described in Example 20, with the fibers perpendicular to the long axis of the sample. The "rough" side of the backing was adjacent the adhesive layer. A 1.8-cm×2.5-cm gauze pad was attached to the adhesive layer in the center of the sample and the holes had been pre-cut such that the rows began 6 mm from each end of the sample.

The FAD sample was evaluated for ease of removal by adhering the sample with finger pressure to the forearm of a human subject, waiting 10 minutes, and then removing by lifting and stretching the gauze pad at about a 90° angle to the plane of the forearm. Very little force was required to stretch the backing and to remove the sample painlessly from the skin and hair of the forearm. During stretching and removal, the backing was observed to break and to delaminate from the adhesive layer.

Example 52

A paper backing (Hammermill Laserprint paper (0.11-mm thick), Product No. 00460-4, International Paper, Memphis, Tenn.)) was perforated with a metal die to provide parallel rows of holes separated by 6.35 cm. The holes were rectangular in shape (1.75-mm×0.07-mm) with the long sides of the holes oriented in the direction of the rows and the space between holes within a row was 0.7 mm.

A FAD sample was made by laminating with thumb pressure at room temperature a strip (2.54-cm×7.6-cm) of the perforated paper backing to a strip (2.54-cm×7.6-cm) of the adhesive described in Example 20, with the fibers perpendicular to the long axis of the sample. A 1.8-cm×2.5-cm gauze pad was attached to the adhesive layer in the center of the sample and the holes had been pre-cut such that the rows began 6 mm from each end of the sample.

The FAD sample was evaluated for ease of removal by adhering the sample with finger pressure to the forearm of a human subject, waiting 10 minutes, and then removing by pulling one end of the sample and stretching the sample at about a 35° angle to the plane of the forearm. Very little force was required to stretch the backing and to remove the sample painlessly from the skin and hair of the forearm. During stretching and removal, the backing was observed to break and to delaminate from the adhesive layer.

Example 53

A stretch removable FAD sample was made by laminating with thumb pressure at room temperature a sheet (10.2-cm square) of a Rayon/Nylon nonwoven backing [thermal spunbond Rayon/Nylon nonwoven fabric, Fiber No. 149-245, basis weight=25 g/m$^2$, Veratec, Walpole, Mass.] to a sheet (10.2-cm square) of the adhesive described in Example 20, with the fibers perpendicular to the long axis of the sample. The sheets were oriented such that the adhesive layer, when subsequently stretched for removal, would be stretched in a direction parallel to the machine direction of the adhesive layer. Prior to lamination, the adhesive sheet was covered along one edge with a strip of paper that could serve as a handle for grasping the adhesive layer alone.

The resulting laminate was cut into a 2.54-cm×7.6-cm FAD sample and adhered with thumb pressure onto a mirror-finished steel plate with the paper handle allowed to extend over the end of the plate. The paper handle of the sample was finger-grasped and stretched in the plane of the adhesive-backing interface at a rate of about 150 cm/min. Upon stretching, the adhesive released from between the plate surface and the backing.

Example 54

A FAD sample was made by laminating with thumb pressure at room temperature a strip (2.54-cm×7.6-cm) of a polypropylene backing [melt-blown nonwoven polypropylene (basis weight 20 g/M$^2$), Kimberly-Clark, Irving, Tex.] to a strip (2.54-cm×7.6-cm) of the adhesive described in Example 20. A 1.3-cm piece of the adhesive/backing laminate was gathered in the middle of the strip in such a way that a fold was made perpendicular to the greatest length of the strip. A 1.8-cm×2.5-cm gauze pad was attached to the adhesive layer in the center of the sample.

The FAD sample was evaluated by adhering the sample with finger pressure to the forearm of a human subject, waiting 10 minutes, and then using the fold in the FAD as a handle, removing by lifting and stretching the gauze pad at about a 90° angle to the plane of the forearm. Very little force was required to stretch the backing and to remove the sample painlessly from the skin and hair of the forearm. During stretching and removal, the backing was observed to break and to delaminate from the adhesive layer.

Example 55

A FAD sample having a center fold and a gauze pad was made as described in Example 46, except that the polyurethane backing (as described in Example 43) was used in place of the polypropylene backing. The sample was evaluated as described in Example 46. During stretching and removal, the backing was observed to delaminate from the adhesive layer.

Example 56

A FAD sample having a center fold and a gauze pad was made as described in Example 46, except that the adhesive described in Example 28 was used as the adhesive. The sample was evaluated and the same results obtained as described in Example 46.

Example 57

A blend of 80 parts of PSA-7 and 20 parts of ATTANE 4202 were mixed in a BRABENDER mixer (C. W. Brabender Instruments, South Hackensack, N.J.) at 140° C. to 150° C. for 8 to 10 minutes. The resulting mixtures were hot melt coated between two release liners at 150° C. using a HAAKE single screw extruder (commercially available from Haake, Inc.; Paramus, N.J.) equipped with a draw die. The resulting PSA film had a thickness of 127 micrometers and was laminated to a PCL backing of thickness listed in Table 30 (prepared by solvent coating a 20% solids solution of PCL in toluene onto a release liner and drying at 70° C. for 10 minutes) to make a tape. The stretch removable properties of the tape was determined as described in the Stretch removable Test Method above except that samples were tested not only in the machine direction but also in the cross web direction and at 45° to the machine direction. The results of the laminated samples as well as the PSA film not laminated to a backing are shown in Table 30.

TABLE 30

| Example | PCL backing thickness (micrometers) | Stretch removable Force in the machine direction (N/dm) | Stretch removable Force in the cross machine direction (N/dm) | Stretch removable Force 45° to machine direction (N/dm) |
|---|---|---|---|---|
| 57-1 | 0 | 18.2 | 9.6 | 13.8 |
| 57-2 | 13 | 37.2 | 30.6 | 36.8 |
| 57-3 | 25 | 39.6 | 21.9 | 25.6 |
| 57-4 | 38 | 36.8 | 26.7 | 32.6 |

Examples 58–62 and Comparative Example C37

The mixtures for Examples 58–62 and Comparative Example C37 were prepared using PSA-10 with the level of ATTANE 4202 shown in Table 31. The adhesive mixtures were compounded using a Werner & Pfleiderer ZSK-30 twin screw extruder (commercially available from Werner & Pfleiderer, Inc.; Ramsey, N.J.) and coated onto the non-microstructured side of the microstructured film described above. The hot-melt extrusion coatings of the adhesive layers were carried out at an extrusion temperature of approximately 150° C. to 160° C. The screws were rotated at approximately 200 to 300 rpm. In all cases the coating thickness was approximately 50 microns (two mils). The web speed was 3.0 to 3.7 meters per minute (10 to 12 feet per minute). The tapes thus prepared were tested according to the 50° C. Heat Aging with Adhesion, Shear Holding and Tack Testing Test Method described above. The results are summarized in Table 32.

TABLE 31

| Example | Level of ATTANE 4202 (weight %) |
|---|---|
| C37 | 0 |
| 58 | 10 |
| 59 | 15 |
| 60 | 20 |
| 61 | 25 |
| 62 | 30 |

TABLE 32

| Example | Average 90° Peel Force of First Tape Sample From Second Tape Sample (N/cm) | 90° Peel Behavior Description | Adhesion (N/cm) | Shear (minutes) |
|---|---|---|---|---|
| C37 | 9.73 | Failure between adhesive and backing | 9.37 | 24,915 |
| 58 | 2.18 | No adhesive failure | 10.9 | 25,192 |
| 59 | 6.51 | Adhesive failure in one of the two samples | 11.1 | 21,896 |
| 60 | 2.60 | No adhesive failure | 11.1 | 14,969 |
| 61 | 2.13 | No adhesive failure | 9.31 | 7,287 |
| 62 | 1.25 | No adhesive failure | 5.68 | 402 |

Examples 63–67 and Comparative Examples C38–C41

Samples of the tapes prepared in Examples 63–67 and Comparative Example C37 as well as the commercially available tapes SCOTCHCAL 3650, Box Sealing Tape 311 and Box Sealing Tape 313 were tested according to the Accelerated Adhesive Flow Test Test Method described above. The data are presented in Table 33.

TABLE 33

| Example Number | Test Sheet Tape | Flow depth after different times at 70° C. (micrometers) | | | | | | | | |
|---|---|---|---|---|---|---|---|---|---|---|
| | | 0.5 hr | 1 hr | 2 hrs | 3 hrs | 4 hrs | 5 hrs | 24 hrs | 48 hrs | 72 hrs |
| C38 | Example C37 | 14.8 | 18.3 | 22.5 | 22.0 | 21.8 | 22 | 21.0* | 20.0* | 22.0* |
| 63 | Example 58 | N/A | 6.3 | 5.0 | 5.8 | N/A | 6.0 | 10.0 | 12.0 | 12.3 |
| 64 | Example 59 | N/A | 4.0 | 4.8 | 5.3 | N/A | 4.8 | 7.8 | 7.5 | 8.3 |
| 65 | Example 60 | N/A | 4.8 | 5.5 | 5.3 | N/A | 6.3 | 6.0 | 6.5 | 5.8 |
| 66 | Example 61 | N/A | N/A | 5.8 | 5.8 | N/A | 5.5 | 6.3 | 6.5 | 6.5 |
| 67 | Example 62 | N/A | N/A | 4.5 | 4.5 | N/A | 4.3 | 5.3 | 5.3 | 4.8 |
| C39 | SCOTCHCAL 3650 | N/A | 11.0 | 9.8 | 10.3 | N/A | 11.8 | 13.0 | 11.8 | 11.8 |
| C40 | Box Sealing Tape 311 | N/A | N/A | 12.0 | N/A | 11.5 | N/A | 14.6 | 20.7 | 20.5 |
| C41 | Box Sealing Tape 313 | N/A | N/A | 9.5 | N/A | 13.5 | N/A | 15.0 | 19.3 | 20.0 |

N/A = Data not available

Examples 68 and Comparative Example C42

Several different adhesives were evaluated for creep compliance and low rate viscosity using the "Steady State Shear Creep" test method described above. The following adhesives were evaluated: Example 68: an adhesive of the invention was prepared as in Example 58 but with 8% by weight of fibers and the final adhesive thickness was 0.005 inches (127 micrometers); and Comparative Example 42 has 50 parts block copolymer and 50 parts Wingtack Plus with no fiberous reinforcing material. The results are shown in Table 34 below.

TABLE 34

| Example | Adhesive | $J_0$ (Pa)$^{-1}$ | $\eta_0$ (Pa-sec) |
|---|---|---|---|
| 68 | Microfibered Block Copolymer Adhesive (Hot Melt) | $4.22 \times 10^{-5}$ | 2.1E7 |
| C42 | Block Copolymer Adhesive (Hot Melt) | $5.78 \times 10^{-4}$ | 1.4E7 |

Various modifications and alterations of the present invention will become apparent to those skilled in the art without departing from the spirit and scope of the invention.

What is claimed is:

1. An adhesive composition comprising
   a pressure sensitive adhesive matrix; and
   a fibrous reinforcing material within the pressure sensitive adhesive matrix;
   wherein at least 50% of the fibers in the fibrous reinforcing material are continuous for at least 5 centimeters and the adhesive composition has a yield strength and a tensile strength, and wherein the tensile strength is about 0.7 MPa or greater, and at least about 150% of thy yield strength.

2. The adhesive composition of claim 1 wherein the adhesive composition has an elongation a break of at least about 50%.

3. The adhesive composition of claim 1 wherein the adhesive composition has an elongation at break of at least about 300%.

4. The adhesive composition of claim 1 wherein the adhesive composition has a tensile strength of about 0.8 MPa or greater.

5. The adhesive composition of claim 1 wherein the adhesive composition has a yield strength of no less than about 0.1 MPa.

6. The adhesive composition of claim 1 wherein the adhesive composition has a yield strength of no less than about 0.2 MPa.

7. The adhesive composition of claim 1 wherein the pressure sensitive adhesive comprises about 60 to about 95 weight % of the adhesive composition and the reinforcing material comprises about 5 to about 40 weight % of the adhesive composition.

8. The adhesive composition of claim 1 wherein the pressure sensitive adhesive comprises about 70 to about 95 weight % of the adhesive composition and the reinforcing material comprises about 5 to about 30 weight % of the adhesive composition.

9. The adhesive composition of claim 1 wherein a ratio of the reinforcing material melt viscosity to the pressure sensitive adhesive melt viscosity is about 0.5 to about 1.2.

10. The adhesive composition a claim 1 wherein the fibrous reinforcing material comprises at least one fiber having a diameter of less than about 5 micrometers.

11. The adhesive composition of claim 1 wherein the fibrous reinforcing material comprises at least one fiber having an aspect ratio of greater than about 1000.

12. The adhesive composition of claim 1 wherein the pressure sensitive adhesive comprises a pressure sensitive adhesive based on at least one of a natural rubber, synthetic rubber, styrene block copolymer, polyvinyl ether, poly(meth)acrylate, polyolefin, silicone or combinations thereof.

13. The adhesive composition of claim 1 wherein the pressure sensitive adhesive comprises a polymer derived from at least one alkyl (meth)acrylate ester monomer selected from isooctyl acrylate, 2-ethyl-hexyl acrylate, and n-butyl acrylate; and at least one co-monomer selected from acrylic acid and acrylamide.

14. The adhesive composition of claim 1 wherein the reinforcing material comprises an elastomer having a yield strength no greater than about 20 MPa and a tensile strength of at least about 150% of the yield strength.

15. The adhesive composition of claim 1 wherein the reinforcing material comprises a semi crystalline polymer.

16. The adhesive composition of claim 1 wherein the reinforcing material has a melting point greater than about 70° C.

17. A substrate at least partially coated with the adhesive composition of claim 1.

18. The substrate of claim 17 wherein the substrate comprises a release liner.

19. A tape comprising
a backing having a first and second side; and
the adhesive composition of claim 1 coated on at least a portion of the first side of the backing.

20. A tape comprising
a backing having a first and second side; and
the adhesive composition of claim 1 coated on at least a portion of the first side of the backing and, optionally, on at least a portion of the second side of the backing.

21. A stretch removable article comprising the adhesive composition of claim 1.

22. The adhesive composition of claim 1 wherein the adhesive composition is stretch removable from a substrate.

23. An adhesive composition comprising
a pressure sensitive adhesive matrix; and
a fibrous reinforcing material, having a melting temperature of no less than about 70° C., within the pressure sensitive adhesive matrix;
wherein the adhesive composition has a yield strength and a tensile strength, and the tensile strength is at least about 150% of the yield strength.

24. An adhesive composition comprising
a pressure sensitive adhesive matrix; and
a uniformly dispersed substantially continuous fiber within the pressure sensitive adhesive matrix wherein the fiber is continuous for at least 5 centimeters.

25. An adhesive composition comprising
a pressure sensitive adhesive matrix; and
a fibrous reinforcing material within the pressure sensitive adhesive matrix;
wherein at least 50% of the fibers in the fibrous reinforcing material are continuous for at least 5 centimeters and the adhesive composition flows less than 13 micrometers after 24 hours in an Accelerated Adhesive Flow Test.

26. The adhesive composition of claim 25 wherein the pressure sensitive adhesive matrix has an intrinsic viscosity of at least about 0.45 dl/g.

27. An adhesive composition comprising
a pressure sensitive adhesive matrix; and
a fibrous reinforcing material within the pressure sensitive adhesive matrix;
wherein at least 50% of the fibers in the fibrous reinforcing material are continuous for at least 5 centimeters and the adhesive composition has a creep compliance of less than $7 \times 10^{-4}$ $Pa^{-1}$ and a viscosity greater than $1 \times 10^6$ Pa·s.

* * * * *

UNITED STATES PATENT AND TRADEMARK OFFICE
CERTIFICATE OF CORRECTION

PATENT NO.    : 6,756,098 B2
DATED         : June 29, 2004
INVENTOR(S)   : Zhou, Zhiming It is certified that error appears in the above-identified patent and that said Letters Patent is hereby corrected as shown below:

Column 21,
Line 7, after "two" insert -- release liners --.
Line 29, delete "Mixtures" and insert in place thereof -- The mixtures --.
Line 54, delete "Example" and insert in place thereof -- Examples --.

Column 23,
Line 5, after "using" insert -- a --.

Column 25,
Line 41, after "ELVAX" delete "240" and insert in place thereof -- 210 --.

Column 29,
Line 49, delete "g/M$^2$" and insert in place thereof -- g/m$^2$ --.

Column 32,
Line 35, delete "thy" and insert in place thereof -- the --.
Line 37, delete "a" and insert in place thereof -- at --.

Column 33,
Line 16, delete "a" and insert in place thereof -- of --.

Signed and Sealed this

Fourteenth Day of December, 2004

JON W. DUDAS
*Director of the United States Patent and Trademark Office*